(12) United States Patent
Delangre et al.

(10) Patent No.: US 11,931,508 B2
(45) Date of Patent: *Mar. 19, 2024

(54) REMOTE DIAGNOSTICS OF RESPIRATORY THERAPY DEVICES

(71) Applicant: RESMED INC., San Diego, CA (US)

(72) Inventors: Peter Delangre, Sydney (AU); Andrew Roderick Bath, Sydney (AU); Paul Frederick Birchall, Sydney (AU); Dawn Rosemary Churchill, Sydney (AU); Graham Stephen Cutcliffe, Sydney (AU); Peter James Dassos, Sydney (AU); Mina Samir Kirollos, Sydney (AU); Rehana Nathwani, Sydney (AU); Chinmayee Somaiya, Sydney (AU); Hayden Thomas Stephenson, Sydney (AU); Bradley Scott Templeton, Sydney (AU); Wendall Eric Trull, San Diego, CA (US); Natalie Zotelo, Sydney (AU)

(73) Assignee: ResMed Inc., San Diego, CA (US)

(*) Notice: Subject to any disclaimer, the term of this patent is extended or adjusted under 35 U.S.C. 154(b) by 10 days.

This patent is subject to a terminal disclaimer.

(21) Appl. No.: 17/575,103

(22) Filed: Jan. 13, 2022

(65) Prior Publication Data

US 2022/0134031 A1    May 5, 2022

Related U.S. Application Data

(63) Continuation of application No. 16/776,194, filed on Jan. 29, 2020, now Pat. No. 11,241,550, which is a (Continued)

(30) Foreign Application Priority Data

May 27, 2014 (AU) ................................ 2014901997

(51) Int. Cl.
*A61M 16/00* (2006.01)
*A61B 5/08* (2006.01)
(Continued)

(52) U.S. Cl.
CPC ....... *A61M 16/0051* (2013.01); *A61B 5/0826* (2013.01); *A61M 16/0069* (2014.02);
(Continued)

(58) Field of Classification Search
CPC .............. A61M 16/00; A61M 16/0051; A61M 16/0069; A61M 16/024; A61M 16/06;
(Continued)

(56) References Cited

U.S. PATENT DOCUMENTS 4,782,832 A   11/1988  Trimble et al.
6,497,655 B1  12/2002  Linberg et al.
(Continued)

FOREIGN PATENT DOCUMENTS

JP    2002291889 A    10/2002
JP    2003527184 A    9/2003
(Continued)

OTHER PUBLICATIONS

Extended European Search Report for EP15 80 0058 dated Dec. 18, 2017. 2 pages.
(Continued)

*Primary Examiner* — Tung S Lau
(74) *Attorney, Agent, or Firm* — Botos Churchill IP Law LLP

(57) ABSTRACT

A system and method is disclosed for performing diagnostics on patient devices (720). The patient devices (720) may include respiratory therapy devices that operate in accordance with instruction sets, such as software or firmware. A server (710) may maintain a database of diagnostic data (718) indicating faults in one or more of a plurality of patient
(Continued)

devices (720). The server (710) may transmit this diagnostic data (718) to one or more computing devices (760), including identification of faults that have occurred. The server (710) may also transmit service data to the plurality of patient devices (720) in order to address the identified faults.

14 Claims, 20 Drawing Sheets

Related U.S. Application Data continuation of application No. 15/313,691, filed as application No. PCT/AU2015/050282 on May 27, 2015, now Pat. No. 10,569,036.

(51) Int. Cl.
| | |
|---|---|
| A61M 16/06 | (2006.01) |
| A61M 16/10 | (2006.01) |
| A61M 16/16 | (2006.01) |
| G06F 11/07 | (2006.01) |
| G16H 20/40 | (2018.01) |
| G16H 40/40 | (2018.01) |
| G16H 40/67 | (2018.01) |
| A61B 5/087 | (2006.01) |

(52) U.S. Cl.
CPC .......... *A61M 16/024* (2017.08); *A61M 16/06* (2013.01); *A61M 16/109* (2014.02); *A61M 16/161* (2014.02); *G06F 11/07* (2013.01); *G16H 20/40* (2018.01); *G16H 40/40* (2018.01); *G16H 40/67* (2018.01); *A61B 5/087* (2013.01); *A61M 2016/0027* (2013.01); *A61M 16/0066* (2013.01); *A61M 16/1055* (2013.01); *A61M 16/107* (2014.02); *A61M 16/16* (2013.01); *A61M 2205/14* (2013.01); *A61M 2205/15* (2013.01); *A61M 2205/3368* (2013.01); *A61M 2205/3584* (2013.01); *A61M 2205/3592* (2013.01); *A61M 2205/42* (2013.01); *A61M 2205/502* (2013.01); *A61M 2205/505* (2013.01); *A61M 2205/60* (2013.01); *A61M 2209/08* (2013.01); *Y02A 90/10* (2018.01)

(58) Field of Classification Search
CPC .............. A61M 16/109; A61M 16/161; A61M 16/0066; A61M 16/1055; A61M 16/107; A61B 5/0826; A61B 5/087; G06F 11/07; G16H 20/40; G16H 40/40; G16H 40/67
See application file for complete search history.

(56) References Cited

U.S. PATENT DOCUMENTS

| | | | | |
|---|---|---|---|---|
| 8,034,002 | B2 * | 10/2011 | Coifman | G16H 40/67 |
| | | | | 600/538 |
| 9,795,752 | B2 * | 10/2017 | Birnkrant | G16H 20/40 |
| 9,895,065 | B2 | 2/2018 | Kraus et al. | |
| 10,569,036 | B2 | 2/2020 | Delangre et al. | |
| 10,661,010 | B1 * | 5/2020 | Tsinberg | A61M 5/14276 |
| 10,702,166 | B1 | 7/2020 | Freeman et al. | |
| 11,056,242 | B1 * | 7/2021 | Jain | G16H 10/60 |
| 11,241,550 | B2 * | 2/2022 | Delangre | A61M 16/024 |
| 2003/0101375 | A1 | 5/2003 | Hohn | |
| 2004/0236240 | A1 | 11/2004 | Kraus et al. | |
| 2005/0197589 | A1 | 9/2005 | Kline | |
| 2006/0085696 | A1 | 4/2006 | Bauer et al. | |
| 2006/0253045 | A1 * | 11/2006 | Coifman | A61B 5/0871 |
| | | | | 600/529 |
| 2007/0010719 | A1 | 1/2007 | Huster et al. | |
| 2007/0078357 | A1 | 4/2007 | Kline | |
| 2009/0044808 | A1 | 2/2009 | Guney et al. | |
| 2009/0063193 | A1 * | 3/2009 | Barton | G08B 21/02 |
| | | | | 340/539.11 |
| 2010/0000534 | A1 | 1/2010 | Kooij et al. | |
| 2010/0078024 | A1 | 4/2010 | Andrieux | |
| 2010/0113958 | A1 | 5/2010 | Casset | |
| 2010/0331711 | A1 | 12/2010 | Krauss et al. | |
| 2012/0035449 | A1 * | 2/2012 | Coifman | A61B 5/0871 |
| | | | | 600/300 |
| 2013/0157571 | A1 | 6/2013 | Wondka et al. | |
| 2013/0185093 | A1 | 7/2013 | Wittliff et al. | |
| 2014/0135640 | A1 | 5/2014 | Kraus et al. | |
| 2015/0013674 | A1 | 1/2015 | Doyle et al. | |
| 2015/0157214 | A1 | 6/2015 | Krauss et al. | |
| 2016/0234686 | A1 | 8/2016 | Bone et al. | |
| 2017/0225036 | A1 * | 8/2017 | Kimishima | G06M 3/08 |
| 2018/0082033 | A1 * | 3/2018 | Meredith | G16H 40/67 |

FOREIGN PATENT DOCUMENTS

| | | |
|---|---|---|
| JP | 2009507534 A | 2/2009 |
| JP | 2010510832 A | 4/2010 |
| WO | 1998004310 A1 | 2/1998 |
| WO | 200170100 A2 | 9/2001 |
| WO | 2004073778 A1 | 9/2004 |
| WO | 2005063328 A1 | 7/2005 |
| WO | 2006074513 A1 | 7/2006 |
| WO | 2006130903 A1 | 12/2006 |
| WO | 2008067176 A1 | 6/2008 |
| WO | 2009021075 A2 | 2/2009 |
| WO | 2009052560 A1 | 4/2009 |
| WO | 2010135785 A1 | 12/2010 |
| WO | 2010141922 A1 | 12/2010 |

OTHER PUBLICATIONS

International Search Report and Written Opinion for Application No. PCT/AU2015/050282 dated Aug. 27, 2015.
Japanese Office Action issued in corresponding Japanese application No. 2020-076454 dated Apr. 13, 2021.
Notice of Allowance for JP Patent Application No. 2020-076454.
Office Action dated May 17, 2019.
Maglogiannis, I., Risk analysis of a patient monitoring system using Bayesian Network modeling, Nov. 15, 2005, p. 637-647.
West, John B, "Respiratory Physiology", Lippincott Williams & Wilkins, 9th edition published 2011.
Notice of Allowance issued in corresponding Japanese Patent Application No. 2021-214565, dated May 23, 2023, 6 pages.

* cited by examiner

REMOTE DIAGNOSTICS OF RESPIRATORY THERAPY DEVICES

1 CROSS-REFERENCES TO RELATED APPLICATIONS

This application is a continuation of U.S. patent application Ser. No. 16/776,194, filed on Jan. 29, 2020, issued as U.S. Pat. No. 11,241,550, which is a continuation of U.S. patent application Ser. No. 15/313,691, filed on Nov. 23, 2016, issued as U.S. Pat. No. 10,569,036, which is a national phase entry under 35 U.S.C. § 371 of International Application No. PCT/AU2015/050282, filed May 27, 2015, published in English, which claims priority from Australian Provisional Application No. 2014901997, filed on May 27, 2014, all of the disclosures of which are hereby incorporated herein by reference.

2 BACKGROUND

2.1 (1) Field of the Technology

The present technology relates to medical devices that may be used in connection with the detection, diagnosis, treatment, prevention and amelioration of respiratory-related disorders.

2.2 (2) Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Some examples of respiratory disorders include: Obstructive Sleep Apnea (OSA), Cheyne Stokes Respiration (CSR), Obesity Hyperventilation Syndrome (OHS), Chronic Obstructive Pulmonary Disease (COPD), Neuromuscular Disease (NMD) or chest wall disorders.

Otherwise healthy individuals may take advantage of systems and devices to prevent respiratory disorders from arising.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilator support to a patient through the upper airways to assist the patient in taking a full breath and/or maintain adequate oxygen levels in the body by doing some or all of the work of breathing. The ventilator support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Systems

A treatment system may comprise a Respiratory Pressure Therapy Device (RPT device), an air circuit, a humidifier, a patient interface, and data management.

2.2.4 Patient Interface

A patient interface may be used to interface respiratory equipment to its user, for example by providing a flow of breathable gas. The flow of breathable gas may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use and uncomfortable especially when worn for long periods of time or when a patient is unfamiliar with a system. For example, masks designed solely for aviators, mask designed as part of personal protection equipment (e.g. filter masks), SCUBA masks or for the administration of anasthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

2.2.4.1 Seal-Forming Portion

Patient interfaces may include a seal-forming portion. Since it is in direct contact with the patient's face, the shape and configuration of the seal-forming portion can have a direct impact the effectiveness and comfort of the patient interface.

A patient interface may be partly characterised according to the design intent of where the seal-forming portion is to engage with the face in use. In one form of patient interface, a seal-forming portion may comprise two sub-portions to engage with respective left and right nares. In one form of patient interface, a seal-forming portion may comprise a single element that surrounds both nares in use. Such single element may be designed to for example overlay an upper lip region and a nasal bridge region of a face. In one form of patient interface a seal-forming portion may comprise an element that surrounds a mouth region in use, e.g. by forming a seal on a lower lip region of a face. In one form of patient interface, a seal-forming portion may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming portion that may be effective in one region of a patient's face may be in appropriate in another region, e.g. because of the different shape, structure, variability and sensitivity regions of the patient's face. For example, a seal on swimming goggles that overlays a patient's forehead may not be appropriate to use on a patient's nose.

Certain seal-forming portions may be designed for mass manufacture such that one design fit and be comfortable and effective for a wide range of different face shapes and sizes. To the extent to which there is a mismatch between the shape of the patient's face, and the seal-forming portion of the mass-manufactured patient interface, one or both must adapt in order for a seal to form.

One type of seal-forming portion extends around the periphery of the patient interface, and is intended to seal against the user's face when force is applied to the patient interface with the seal-forming portion in confronting engagement with the user's face. The seal-forming portion may include an air or fluid filled cushion, or a moulded or formed surface of a resilient seal element made of an elastomer such as a rubber. With this type of seal-forming portion, if the fit is not adequate, there will be gaps between the seal-forming portion and the face, and additional force will be required to force the patient interface against the face in order to achieve a seal.

Another type of seal-forming portion incorporates a flap seal of thin material so positioned about the periphery of the mask so as to provide a self-sealing action against the face of the user when positive pressure is applied within the mask. Like the previous style of seal forming portion, if the match between the face and the mask is not good, additional force may be required to affect a seal, or the mask may leak. Furthermore, if the shape of the seal-forming portion does not match that of the patient, it may crease or buckle in use, giving rise to leaks.

Another type of seal-forming portion may comprise a friction-fit element, e.g. for insertion into a naris.

Another form of seal-forming portion may use adhesive to affect a seal. Some patients may find it inconvenient to constantly apply and remove an adhesive to their face.

A range of patient interface seal-forming portion technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT nasal pillows mask, SWIFT II nasal pillows mask, SWIFT LT nasal pillows mask, SWIFT FX nasal pillows mask and LIBERTY full-face mask. The following patent applications, assigned to ResMed Limited, describe nasal pillows masks: International Patent Application WO2004/073,778 (describing amongst other things aspects of ResMed SWIFT nasal pillows), US Patent Application 2009/0044808 (describing amongst other things aspects of ResMed SWIFT LT nasal pillows); International Patent Applications WO 2005/063,328 and WO 2006/130,903 (describing amongst other things aspects of ResMed LIBERTY full-face mask); International Patent Application WO 2009/052,560 (describing amongst other things aspects of ResMed SWIFT FX nasal pillows).

2.2.4.2 Positioning and Stabilising

A seal-forming portion of a patient interface used for positive air pressure therapy is subject to the corresponding force of the air pressure to disrupt a seal. Thus a variety of techniques have been used to position the seal-forming portion, and to maintain it in sealing relation with the appropriate portion of the face.

One technique is the use of adhesives. See for example US Patent publication US 2010/0000534.

Another technique is the use of one or more straps and stabilising harnesses. Many such harnesses suffer from being one or more of ill-fitting, bulky, uncomfortable and awkward to use.

2.2.5 Respiratory Pressure Therapy (RPT) Device

One known RPT device used for treating sleep disordered breathing is the S9 Sleep Therapy System, manufactured by ResMed. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD. RPT devices have also been known as flow generators.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit.

RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

RPT devices typically also include an inlet filter, various sensors and a microprocessor-based controller. A blower may include a servo-controlled motor, a volute and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with expiration despite the inertia. In some cases the pressure generator may also include a valve capable of discharging generated air to atmosphere as a means for altering the pressure delivered to the patient as an alternative to motor speed control. The sensors measure, amongst other things, motor speed, mass flow rate and outlet pressure, such as with a pressure transducer or the like. The controller may include data storage capacity with or without integrated data retrieval and display functions.

Table of noise output levels of prior devices (one specimen only, measured using test method specified in ISO3744 in CPAP mode at 10 cmH$_2$O).

| Device name | A-weighted sound power level dB(A) | Year (approx.) |
|---|---|---|
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

2.2.6 Humidifier

Delivery of a flow of breathable gas without humidification may cause drying of airways. Medical humidifiers are used to increase humidity and/or temperature of the flow of breathable gas in relation to ambient air when required, typically where the patient may be asleep or resting (e.g. at a hospital). As a result, a medical humidifier is preferably small for bedside placement, and it is preferably configured to only humidify and/or heat the flow of breathable gas delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a flow generator or RPT device and the patient interface produces humidified gas that minimizes drying of the nasal mucosa and increases patient airway comfort. In addition, in cooler climates warm air applied generally to the face area in and about the patient interface is more comfortable than cold air.

Respiratory humidifiers are available in many forms and may be a standalone device that is coupled to a respiratory apparatus via an air circuit, is integrated with or configured to be coupled to the relevant respiratory apparatus. While known passive humidifiers can provide some relief, generally a heated humidifier may be used to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator or RPT device, and a gas outlet adapted to be connected to an air circuit that delivers the humidified gas to the patient interface.

Heated passover humidification is one common form of humidification used with a RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 CPAP devices respectively.

Other humidifiers may also be used such as a bubble or diffuser humidifier, a jet humidifier or a wicking humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier. A wicking humidifier uses a water absorbing material, such as sponge or paper, to absorb water by capillary action. The water absorbing material is placed within or adjacent at least a portion of the air flow path to allow evaporation of the water in the absorbing material to be taken up into the air flow.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

3 BRIEF SUMMARY OF THE TECHNOLOGY

Aspects of the disclosure provide a computer implemented method performing remote diagnostics in connection with a plurality of patient devices. The method may include receiving and storing diagnostic data from a plurality of patient devices, wherein the diagnostic data identifies the presence of a fault in connection with at least one of the plurality of patient devices. The method may also include receiving a query for a first portion of the diagnostic data for a first patient device, and identifying the presence of a fault based on the first portion of the diagnostic data. In addition, the method may include transmitting the first portion of the diagnostic data or the identified presence of a fault, in response to the received query, wherein the first portion of the diagnostic data identifies the presence of a fault associated with the first patient device. The method may still further include receiving identification of service data to be transmitted to the first patient device, wherein at least a portion of the service data addresses one or more identified faults. The identified service data may then be transmitted to the first patient device.

The method for diagnostic monitoring of medical devices may also comprise: receiving, by one or more processors, diagnostic data from a plurality of patient devices, wherein the diagnostic data identifies one or more faults in connection with at least one of the plurality of patient devices; storing, by the one or more processors, the received diagnostic data; identifying, by the one or more processors, the presence of a fault associated with a first portion of the diagnostic data; transmitting, by the one or more processors, at least one of the first portion of the diagnostic data and an identified fault in connection with at least one of the plurality of patient devices to a remote computing device; and transmitting, by the one or more processors, service data identified on the basis of at least one of the first portion of the diagnostic data and the one or more identified faults, to the at least one of the plurality of patient devices. The method may further comprise receiving, in response to transmitting at least the first portion of the diagnostic data to the remote computing device by the one or more processors, identification of the service data to be transmitted to the at least one of the plurality of patient devices, wherein at least a portion of the service data addresses the one or more identified faults. It should be noted that the expression "indication of the presence of a fault" used throughout the text of this disclosure should be considered to also include an indication that a fault is likely to occur in a specific device, as well as an indication that no fault is currently present in any of the devices.

In accordance with one aspect, the first patient device comprises a respiratory pressure therapy device. In addition, the diagnostic data may be received based on the occurrence of a triggering event and may be comprised of therapeutic settings of the patient device. The diagnostic data may also comprise a log of operations and faults that have occurred in connection with the patient device.

The disclosed method may also include receiving an indication from the first patient device that the service data was successfully transmitted and updating the diagnostic data to indicate implementation of the first service data.

In accordance with one aspect, the presence of a fault may be identified based on one or more components of the first patient device in which a fault has occurred. In addition, the query may further include a request for diagnostic data for the plurality patient devices, and transmitting the first portion of the diagnostic data may include transmitting diagnostic data for the plurality of patient devices.

Another disclosed method may include a patient device that collects diagnostic data relating to the operation of the patient device, wherein the diagnostic data identifies the presence of a fault that has occurred in connection with the patient device. The patient device may also determine whether a triggering event has occurred for which the diagnostic data is to be transmitted over a network. If a triggering event has occurred, the patient device may transmit the diagnostic data over the network. The patient device may also receive service data that addresses an identified fault and performing one or more operations in accordance with the received service data.

In accordance with one aspect, the triggering event may be based on a plurality of conditions being met before the diagnostic data is transmitted. The triggering event may also be based on a patient having finished using the patient device for a predetermined period of time. The triggering event may also be based on a schedule for which diagnostic data is to be transmitted.

The service data may include a first portion and a second portion, wherein a first component of the patient device operates in accordance with the first portion of the service data and a second component operates in accordance with the second portion of the service data. In accordance with one aspect, at least a portion of the diagnostic data may relate to at least one of a patient's apnea index, hypopnea index, and apnea-hypopnea index.

In another aspect, the service data may include a command to adjust one or more settings of the patient device, and the diagnostic data may identify one or more settings of the patient device at a time at which the fault occurred. The identified fault may be provided as an icon for display on the remote computing device, and the icon may have a variable appearance that varies based on the type of fault that has occurred. In addition, transmitting the identified fault may include providing usage icons for display on the remote computing device, wherein the usage icons indicate an extent to which the patient device was used.

The disclosure also provides for a system that includes a one or more computing devices configured to perform the methods described herein.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, in the form of nasal pillows, receives a supply of air at positive pressure from a RPT device 4000. Air from the RPT device is humidified in a humidifier 5000, and passes along an air circuit 4170 to the patient 1000.

4.2 THERAPY

4.2.1 Respiratory System

Figure 2A:
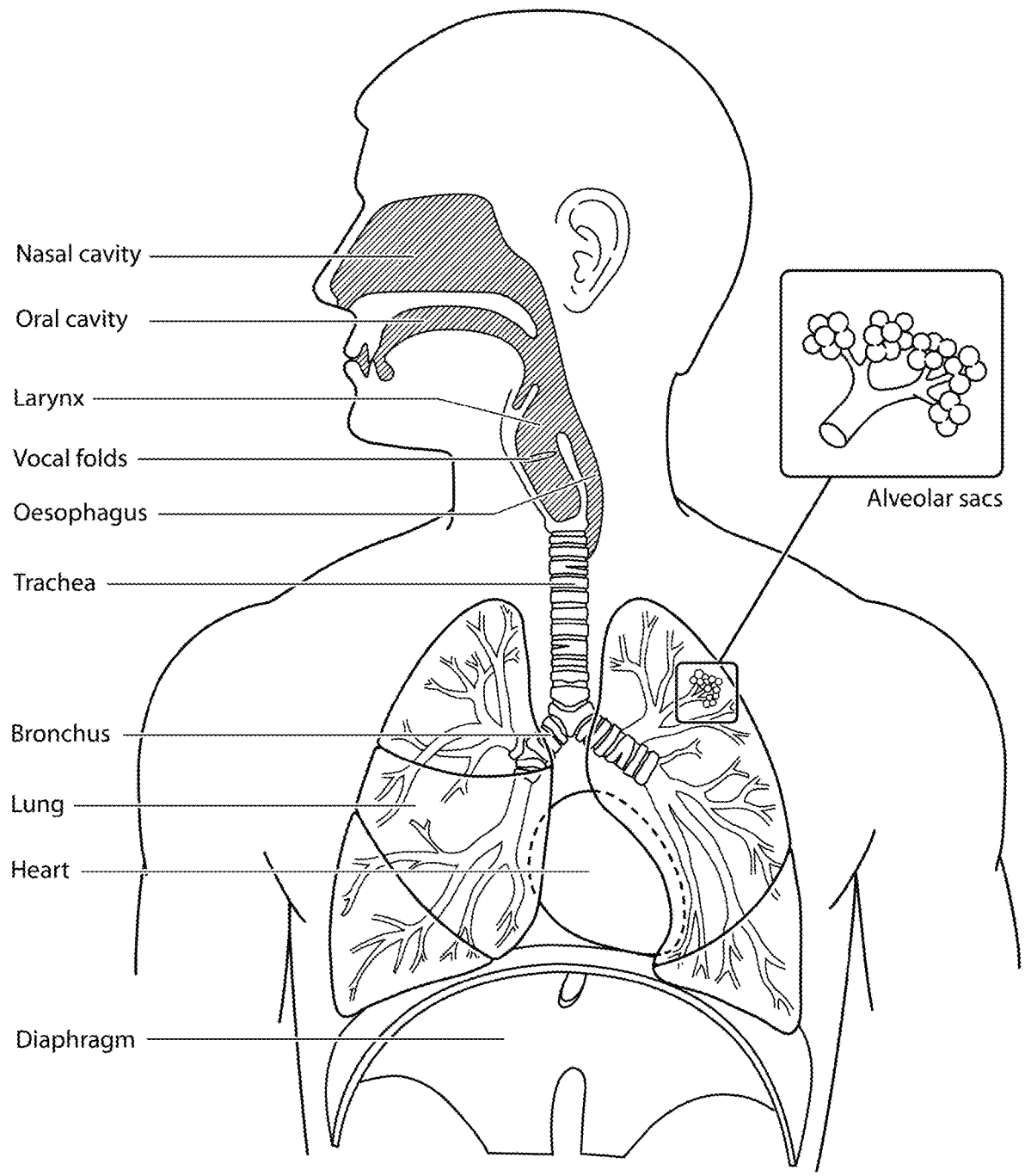

FIG. 2a shows an overview of a human respiratory system including the nasal and oral cavities, the larynx, vocal folds, oesophagus, trachea, bronchus, lung, alveolar sacs, heart and diaphragm.

Figure 2B:
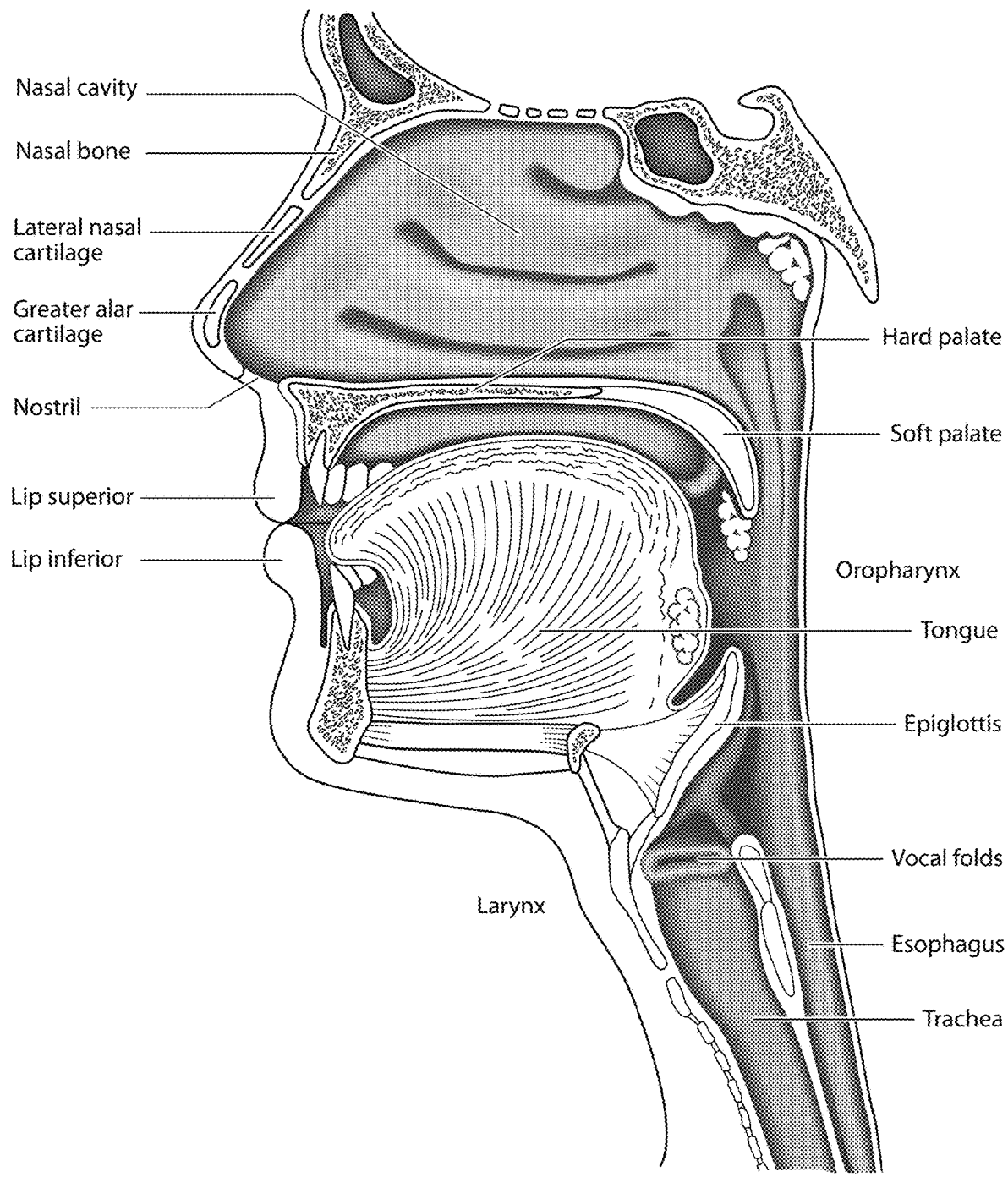

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.2.2 Facial Anatomy

Figure 2C:
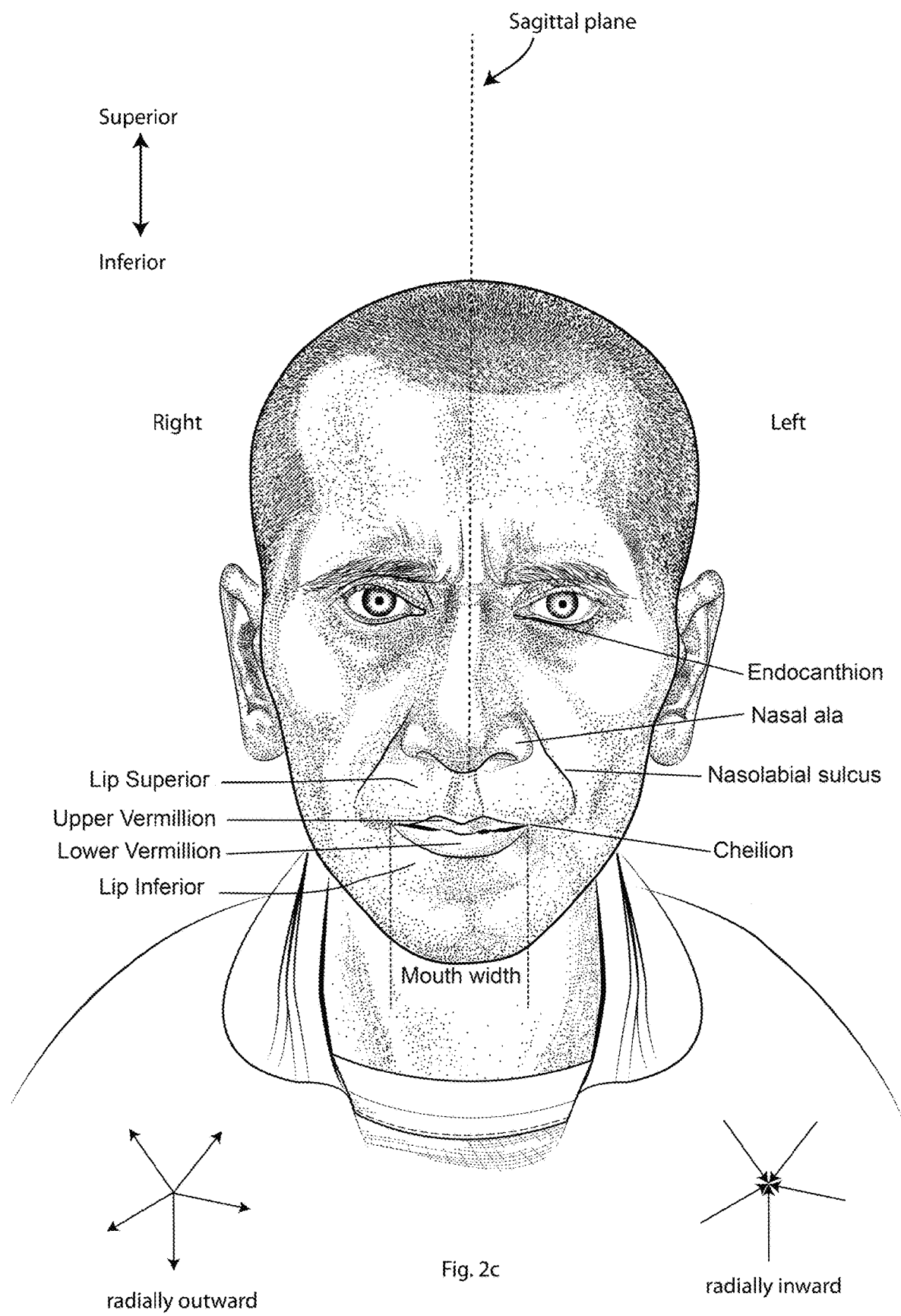

FIG. 2c is a front view of a face with several features of surface anatomy identified including the lip superior, upper vermillion, lower vermillion, lip inferior, mouth width, endocanthion, a nasal ala, nasolabial sulcus and cheilion.

4.3 Patient Interface

Figure 3A:
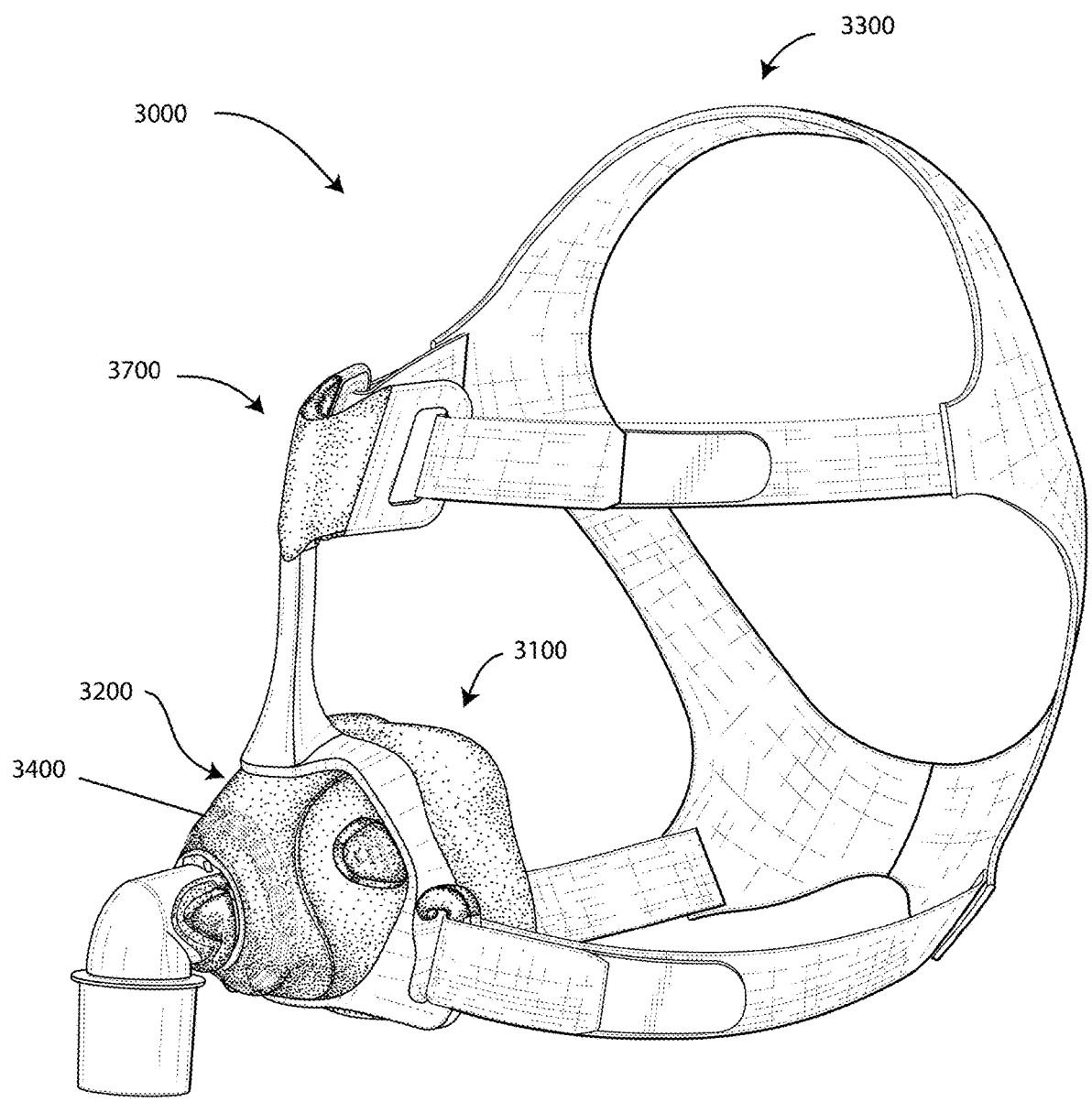

FIG. 3a shows an example of a patient interface known in the prior art.

4.4 Respiratory Pressure Therapy (RPT) Device

Figure 4A:
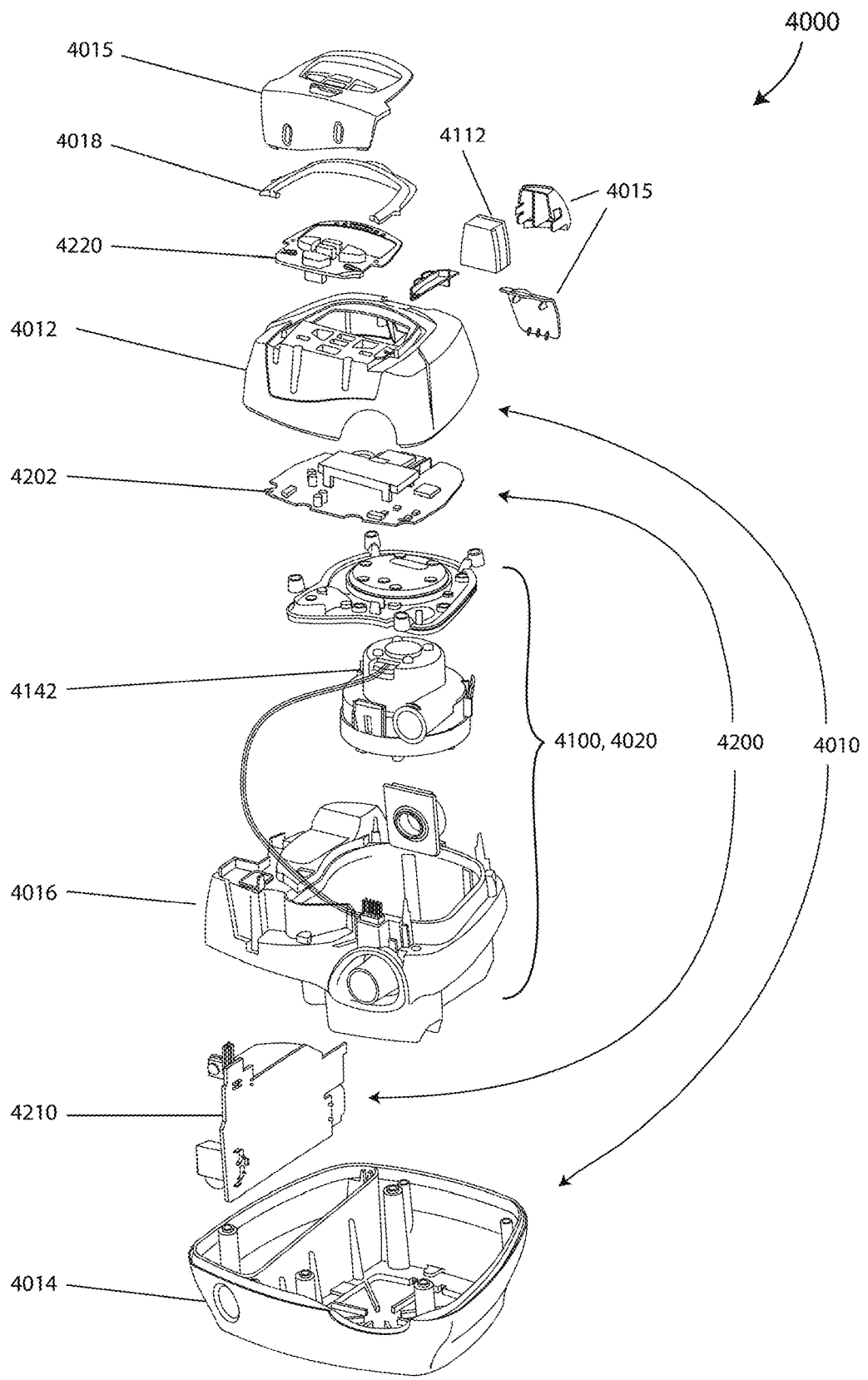

FIG. 4a shows a RPT device in accordance with one form of the present technology.

Figure 4B:
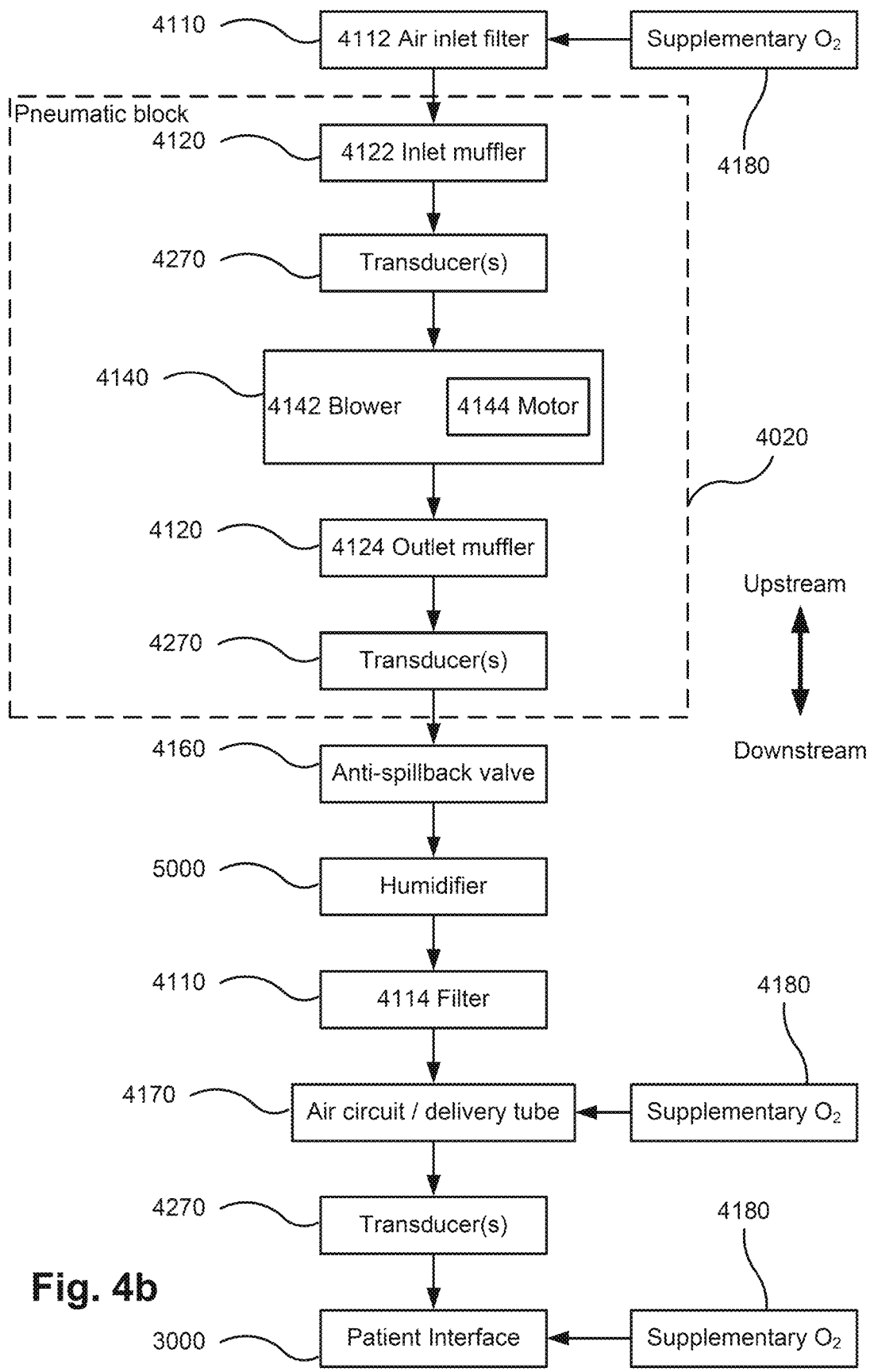

FIG. 4b shows a schematic diagram of the pneumatic circuit of a RPT device in accordance with one form of the present technology. The directions of upstream and downstream are indicated.

Figure 4C:
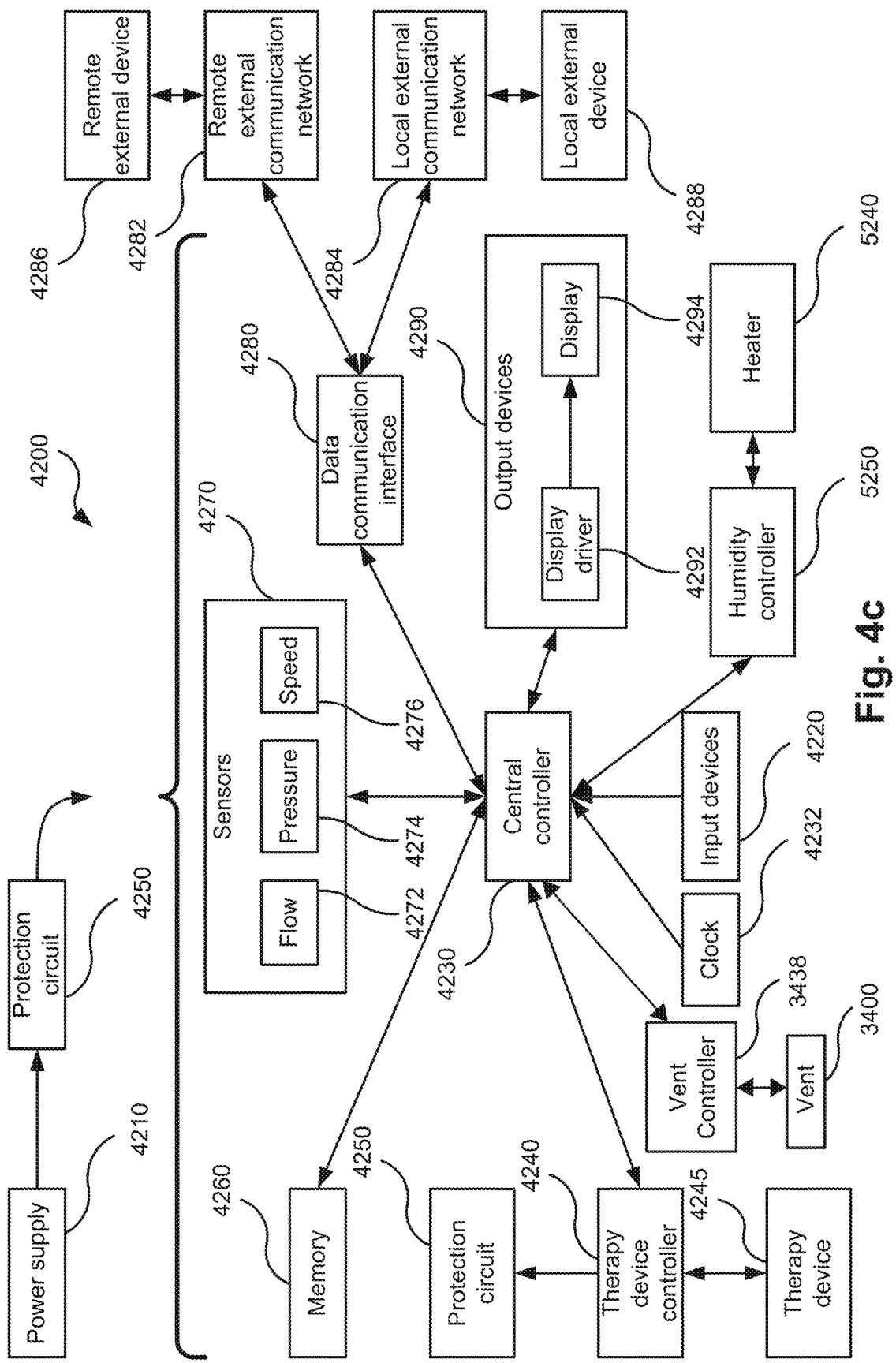

FIG. 4c shows a schematic diagram of the electrical components of a RPT device in accordance with one aspect of the present technology.

4.5 Humidifier

Figure 5A:
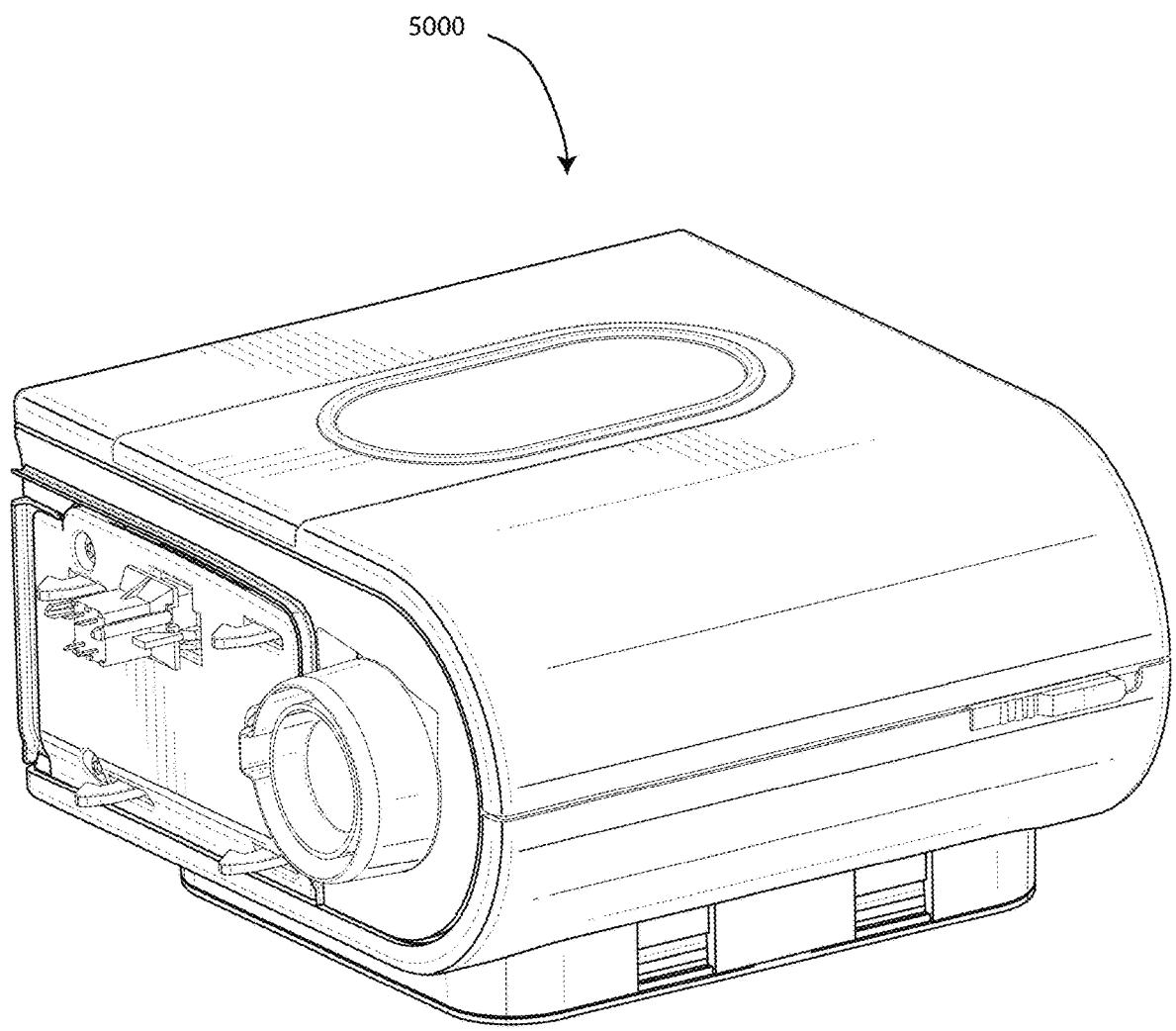

FIG. 5a shows a humidifier in accordance with one aspect of the present technology.

4.6 Breathing Waveforms

Figure 6A:
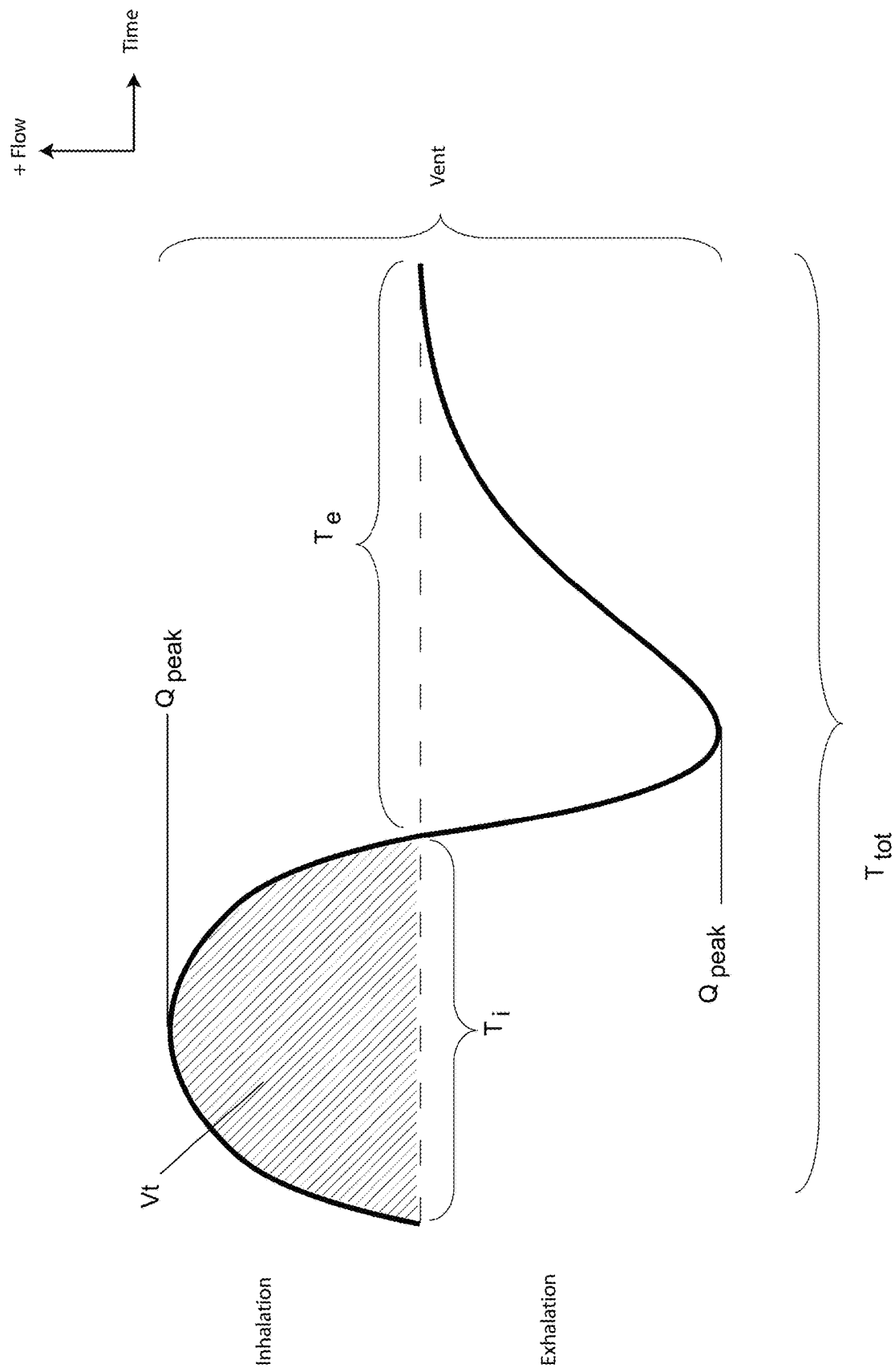

FIG. 6a shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

4.7 Diagnostic System

Figure 7:
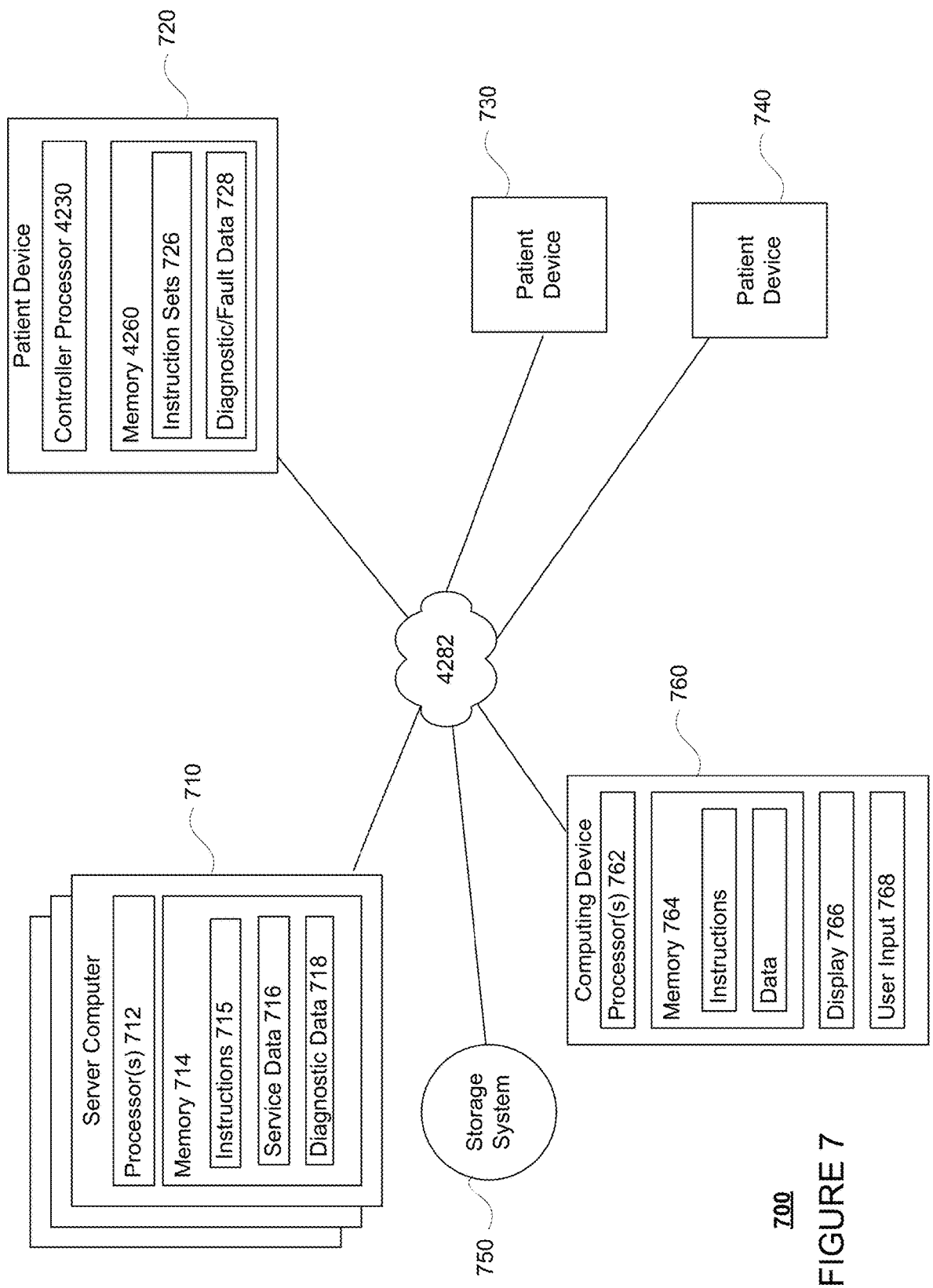
Figure 13:
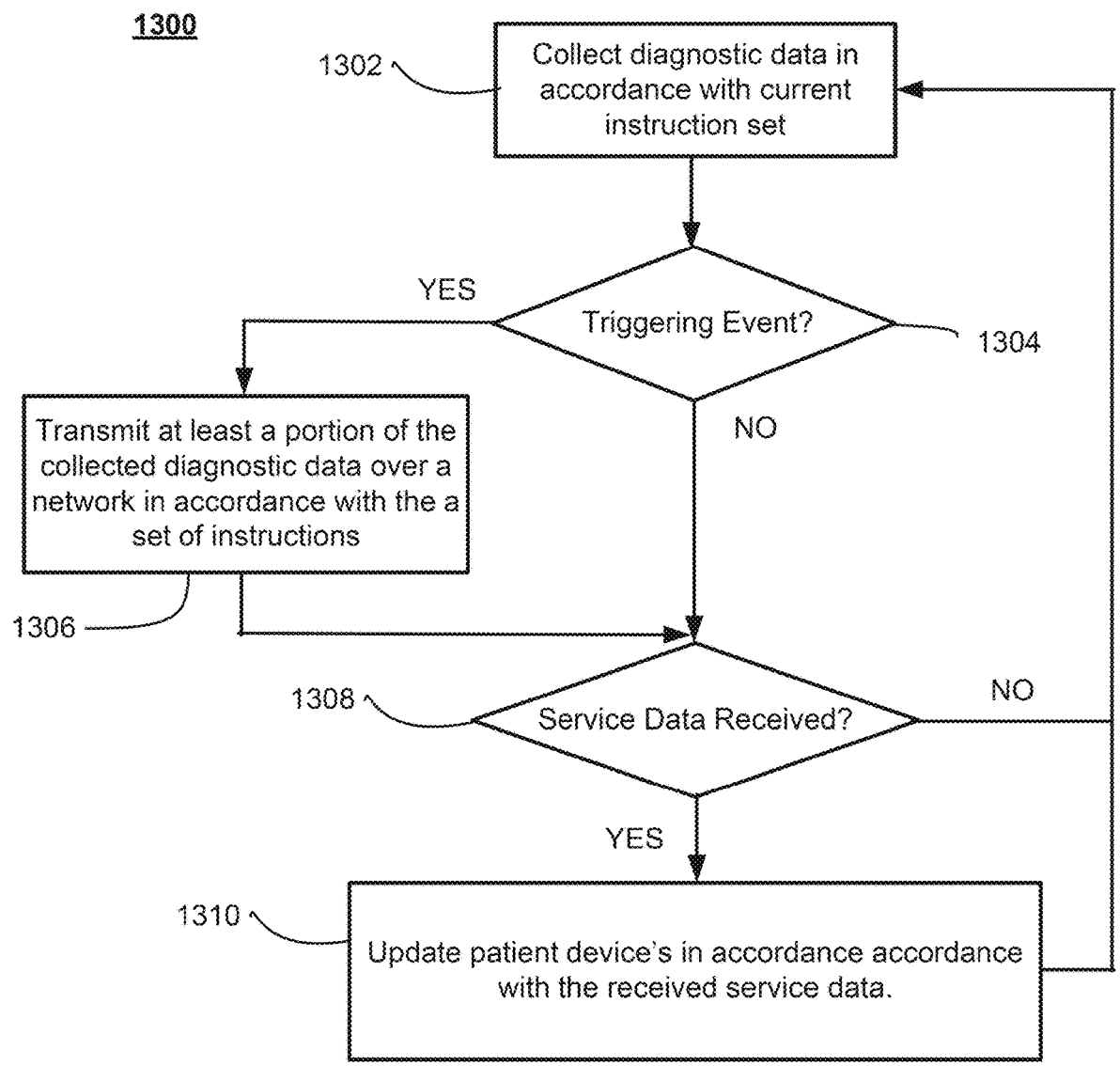
Figure 14:
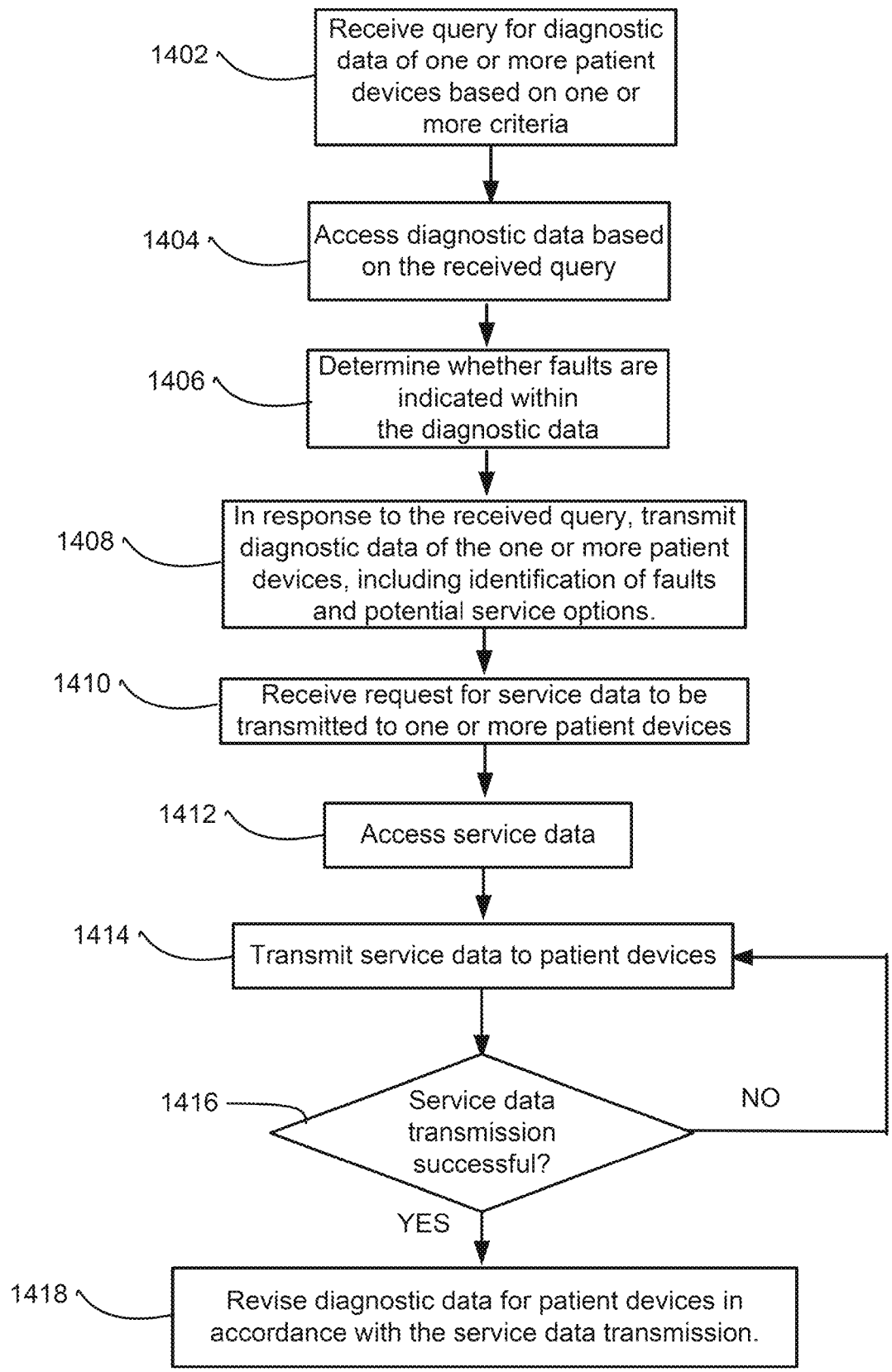

FIG. 7 shows an example communications system 700 that may be used in monitoring and servicing patient devices. Each patient device 720 may comprise an RPT 4000, humidifier 5000, and patient interface 3000. FIGS. 8-12 show webpages that may be displayed in accordance with aspects of the disclosure. FIG. 13 shows flow diagram 1300 of operations that may be performed by patient devices disclosed herein in connection with disclosed methods. FIG. 14 shows flow diagram 1400 for operations that may be performed by computing devices, such as servers, disclosed herein.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Treatment Systems

In one form, the present technology comprises apparatus for treating a respiratory disorder. The apparatus may comprise a flow generator or blower for supplying pressurised respiratory gas, such as air, to the patient 1000 via an air delivery tube leading to a patient interface 3000.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

5.3 Patient Interface 3000

A non-invasive patient interface 3000 in accordance with one aspect of the present technology comprises the following functional aspects: a seal-forming structure 3100, a plenum chamber 3200, a positioning and stabilising structure 3300, a vent 3400 and a connection port 3600 for connection to air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.3.1 Seal-Forming Structure 3100

In one form of the present technology, a seal-forming structure 3100 provides a sealing-forming surface, and may additionally provide a cushioning function.

A seal-forming structure 3100 in accordance with the present technology may be constructed from a soft, flexible, resilient material such as silicone.

In one form, the seal-forming structure 3100 comprises a sealing flange and a support flange. Preferably the sealing flange comprises a relatively thin member with a thickness of less than about 1 mm, for example about 0.25 mm to about 0.45 mm, that extends around the perimeter 3210 of the plenum chamber 3200. Support flange may be relatively thicker than the sealing flange. The support flange is disposed between the sealing flange and the marginal edge of the plenum chamber 3200, and extends at least part of the way around the perimeter 3210. The support flange is or includes a spring-like element and functions to support the sealing flange from buckling in use. In use the sealing flange can readily respond to system pressure in the plenum chamber 3200 acting on its underside to urge it into tight sealing engagement with the face.

In one form the seal-forming portion of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose; a stalk, a flexible region on the underside of the cone and connecting the cone to the stalk. In addition, the structure to which the nasal pillow of the present technology is connected includes a flexible region adjacent the base of the stalk. The flexible regions can act in concert to facilitate a universal joint structure that is accommodating of relative movement—both displacement and angular—of the frusto-cone and the structure to which the nasal pillow is connected. For example, the frusto-cone may be axially displaced towards the structure to which the stalk is connected.

In one form the non-invasive patient interface 3000 comprises a seal-forming portion that forms a seal in use on an upper lip region (that is, the lip superior) of the patient's face.

In one form the non-invasive patient interface 3000 comprises a seal-forming portion that forms a seal in use on a chin-region of the patient's face.

5.3.2 Plenum Chamber 3200

Preferably the plenum chamber 3200 has a perimeter 3210 that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. Preferably the seal-forming structure 3100 extends in use about the entire perimeter 3210 of the plenum chamber 3200.

Figure 1A:
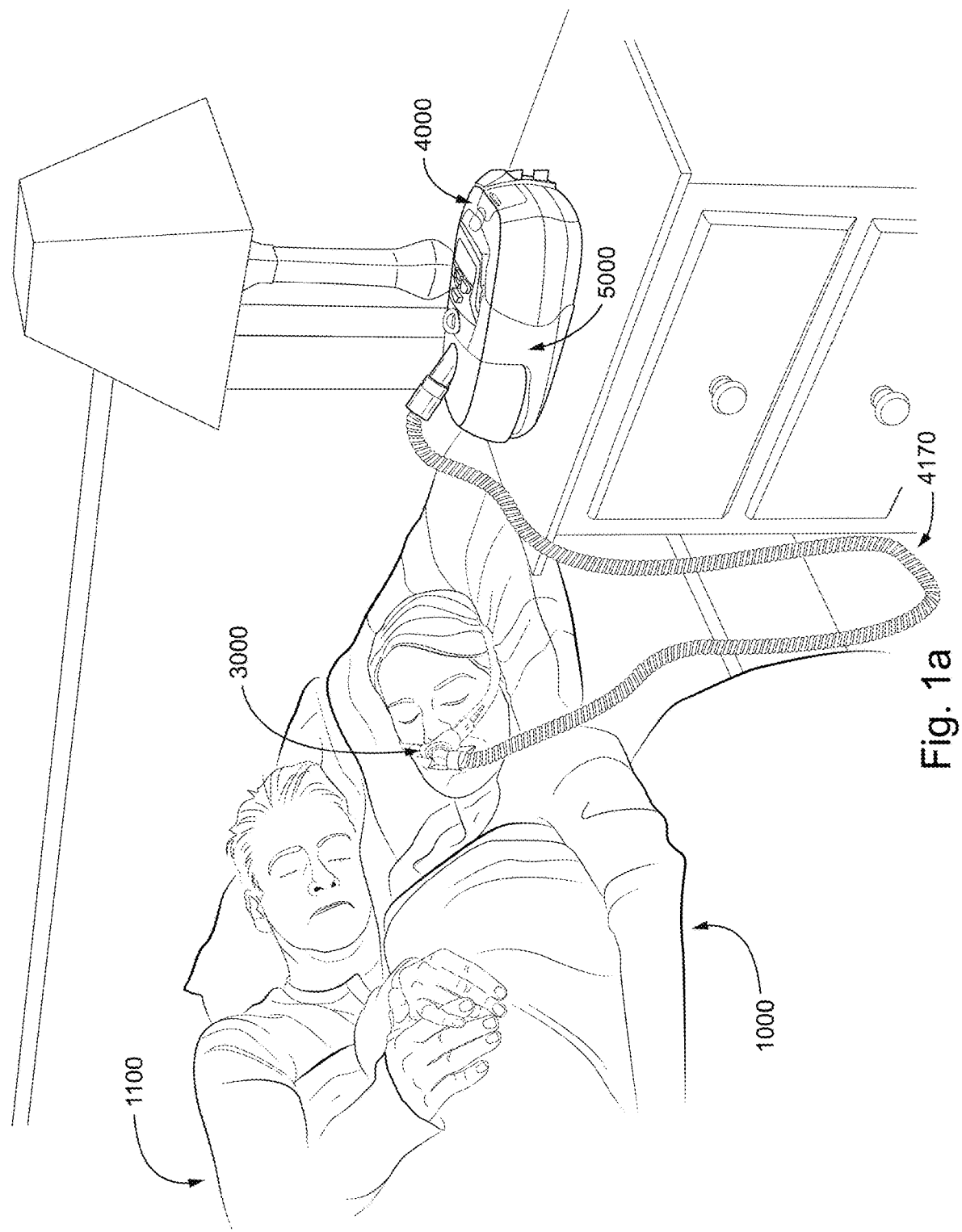
FIG. 1b shows a system including a patient 1000 wearing a patient interface 3000, in the form of a nasal mask, receives a supply of air at positive pressure from a RPT device 4000. Air from the RPT device is humidified in a humidifier 5000, and passes along an air circuit 4170 to the patient 1000.
FIG. 1c shows a system including a patient 1000 wearing a patient interface 3000, in the form of a full-face mask, receives a supply of air at positive pressure from a RPT device. Air from the RPT device is humidified in a humidifier 5000, and passes along an air circuit 4170 to the patient 1000.
Figure 1B:
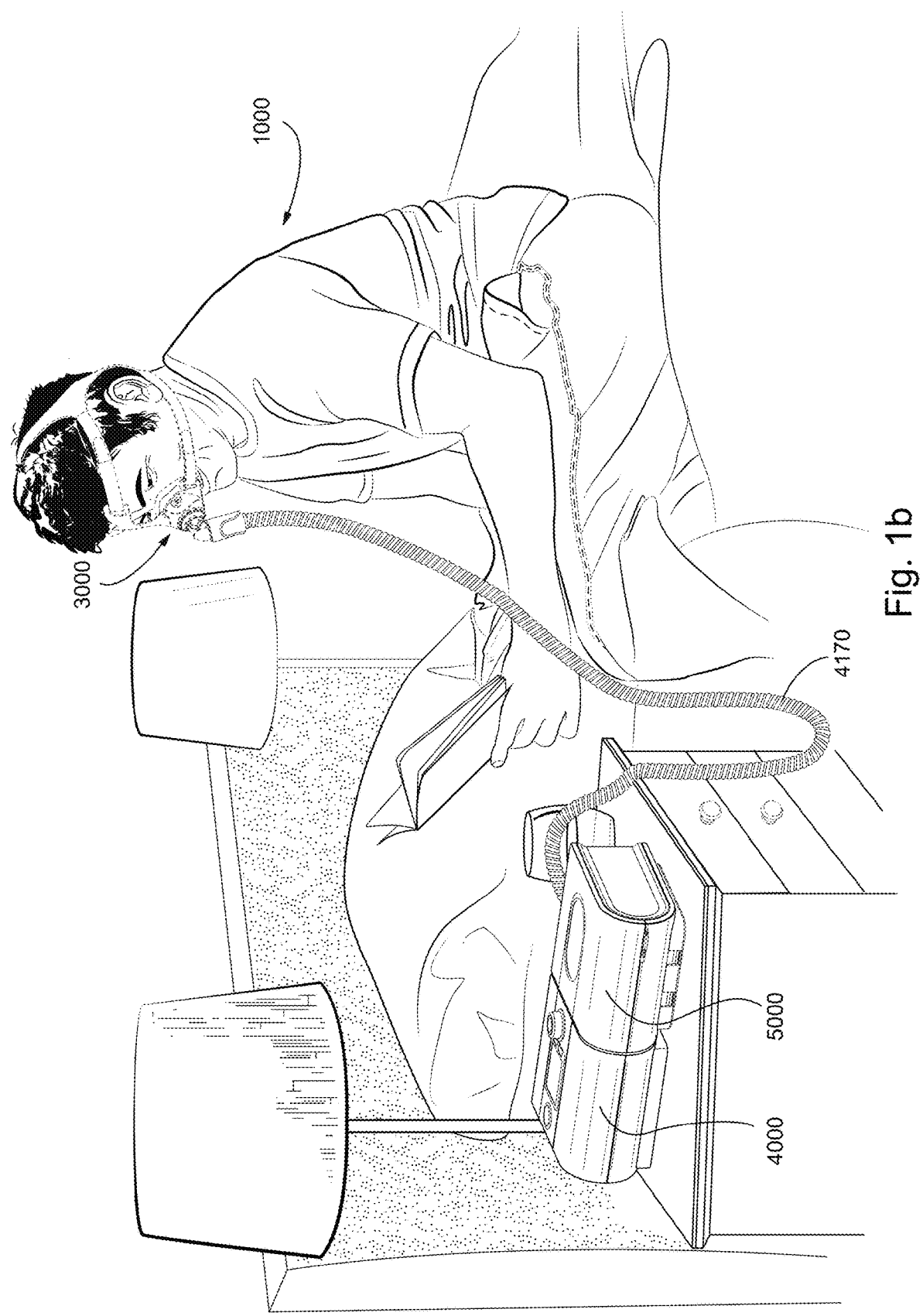
Figure 1C:

In one form, the plenum chamber 3200 may surround and/or be in fluid communication with the nares of the patient where the plenum chamber 3200 is a part of a nasal mask (e.g. shown in FIG. 1b). In another form, the plenum chamber 3200 may surround and/or be in fluid communication with the nares and the mouth of the patient where the plenum chamber 3200 is a part of a full-face mask (e.g., shown in FIG. 1c). In yet another form, the plenum chamber 3200 may engage and/or be in fluid communication with one or more of the nares of the patient where the plenum chamber 3200 is a part of nasal pillows (e.g., shown in FIG. 29).

5.3.3 Positioning and Stabilising Structure 3300

Preferably the seal-forming structure 3100 of the patient interface 3000 of the present technology is held in sealing position in use by the positioning and stabilising structure 3300.

5.4 RPT Device 4000

An example RPT device 4000 that may be suitable for implementing aspects of the present technology may include mechanical and pneumatic components 4100, electrical components 4200 and may be programmed to execute one or more of the control methodologies or algorithms described throughout this specification. The RPT device may have an external housing 4010, preferably formed in two parts, an upper portion 4012 of the external housing 4010, and a lower portion 4014 of the external housing 4010. In alternative forms, the external housing 4010 may include one or more panel(s) 4015. Preferably the RPT device 4000 comprises a chassis 4016 that supports one or more internal components of the RPT device 4000. In one form a pneumatic block 4020 is supported by, or formed as part of the chassis 4016. The RPT device 4000 may include a handle 4018.

The pneumatic path of the RPT device 4000 preferably comprises an inlet air filter 4112, an inlet muffler 4122, a controllable pressure device 4140 capable of supplying air at positive pressure (preferably a blower 4142), and an outlet muffler 4124. One or more pressure sensors 4272 and flow sensors 4274 are included in the pneumatic path.

The preferred pneumatic block 4020 comprises a portion of the pneumatic path that is located within the external housing 4010.

The RPT device 4000 preferably has an electrical power supply 4210, one or more input devices 4220, a central controller 4230, a therapy device controller 4240 and/or any of the controllers previously described, a pressure device 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

The central controller 4230 of the RPT device 4000, which may include one or more processors, can be programmed to execute one or more algorithm modules, preferably including a pre-processing module, a therapy engine module, a pressure control module, and further preferably a fault condition module. It may further include a vent control module that may be configured with one or more of the vent control methodologies described throughout this specification.

5.4.1 RPT Device Mechanical & Pneumatic Components 4100

5.4.1.1 Air Filter(s) 4110

A RPT device in accordance with one form of the present technology may include an air filter 4110, or a plurality of air filters 4110.

In one form, an inlet air filter 4112 is located at the beginning of the pneumatic path upstream of a blower 4142. See FIG. 4b.

In one form, an outlet air filter 4114, for example an antibacterial filter, is located between an outlet of the pneumatic block 4020 and a patient interface 3000. See FIG. 4b.

5.4.1.2 Muffler(s) 4120

In one form of the present technology, an inlet muffler 4122 is located in the pneumatic path upstream of a blower 4142. See FIG. 4b.

In one form of the present technology, an outlet muffler 4124 is located in the pneumatic path between the blower 4142 and a patient interface 3000. See FIG. 4b.

5.4.1.3 Pressure Device 4140

In a preferred form of the present technology, a pressure device 4140 for producing a flow of air at positive pressure is a controllable blower 4142. For example the blower may include a brushless DC motor 4144 with one or more impellers housed in a volute. The blower may be preferably capable of delivering a supply of air, for example about 120 litres/minute, at a positive pressure in a range from about 4 cmH$_2$O to about 20 cmH$_2$O, or in other forms up to about 30 cmH$_2$O.

The pressure device 4140 is under the control of the therapy device controller 4240.

5.4.1.4 Transducer(s) 4270

In one form of the present technology, one or more transducers 4270 are located upstream of the pressure device 4140. The one or more transducers 4270 are constructed and arranged to measure properties of the air at that point in the pneumatic path.

In one form of the present technology, one or more transducers 4270 are located downstream of the pressure device 4140, and upstream of the air circuit 4170. The one or more transducers 4270 are constructed and arranged to measure properties of the air at that point in the pneumatic path.

In one form of the present technology, one or more transducers 4270 are located proximate to the patient interface 3000.

5.4.1.5 Anti-Spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.6 Air Circuit 4170

An air circuit 4170 in accordance with an aspect of the present technology is constructed and arranged to allow a flow of air or breathable gasses between the pneumatic block 4020 and the patient interface 3000.

5.4.1.7 Oxygen Delivery

In one form of the present technology, supplemental oxygen 4180 is delivered to a point in the pneumatic path.

In one form of the present technology, supplemental oxygen 4180 is delivered upstream of the pneumatic block 4020.

In one form of the present technology, supplemental oxygen 4180 is delivered to the air circuit 4170.

In one form of the present technology, supplemental oxygen 4180 is delivered to the patient interface 3000.

5.4.2 RPT Device Electrical Components 4200

5.4.2.1 Power Supply 4210

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000. The power supply may also optionally provide power to any actuator, controller and/or sensors for a vent arrangement as described throughout this specification

5.4.2.2 Input Devices 4220

In one form of the present technology, a RPT device 4000 includes one or more input devices 4220 in the form of buttons, switches or dials to allow a person to interact with the device. These may be implemented for entering settings for operation of the components of the RPT device such as the vent arrangement. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.3 Central Controller 4230

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. In another form, the central controller 4230 comprises discrete electronic components.

In another form of the present technology, the central controller 4230 is a processor suitable to control a RPT device 4000 such as an x86 INTEL processor.

A processor of a central controller 4230 suitable to control a RPT device 4000 in accordance with another form of the present technology includes a processor based on ARM Cortex-M processor from ARM Holdings. For example, an STM32 series microcontroller from ST MICROELECTRONICS may be used.

Another processor suitable to control a RPT device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor for the RPT device 4000. For example a processor from the MSP430 family of microcontrollers, manufactured by TEXAS INSTRUMENTS, may be used.

The processor is configured to receive input signal(s) from one or more transducers 4270, and one or more input devices 4220.

The processor is configured to provide output signal(s) to one or more of an output device 4290, a therapy device controller 4240, a data communication interface 4280 and humidifier controller 5250.

In some forms of the present technology, the processor of the central controller 4230, or multiple such processors, is configured to implement the one or more methodologies described herein such as the one or more algorithms 4300 expressed as computer programs stored in a non-transitory computer readable storage medium, such as memory 4260. In some cases, as previously discussed, such processor(s) may be integrated with a RPT device 4000. However, in some forms of the present technology the processor(s) may be implemented discretely from the flow generation components of the RPT device 4000, such as for purpose of performing any of the methodologies described herein without directly controlling delivery of a respiratory treatment. For example, such a processor may perform any of the methodologies described herein for purposes of determining control settings for a ventilator or other respiratory related events by analysis of stored data such as from any of the sensors described herein. Similarly, such a processor may perform any of the methodologies described herein for purposes controlling operation of any vent arrangement described in this specification.

5.4.2.4 Clock 4232

Preferably RPT device 4000 includes a clock 4232 that is connected to processor.

5.4.2.5 Therapy Device Controller 4240

In one form of the present technology, therapy device controller 4240 is a pressure control module 4330 that forms part of the algorithms 4300 executed by the processor of the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits 4250

Preferably a RPT device 4000 in accordance with the present technology comprises one or more protection circuits 4250.

One form of protection circuit 4250 in accordance with the present technology is an electrical protection circuit.

One form of protection circuit 4250 in accordance with the present technology is a temperature or pressure safety circuit.

5.4.2.7 Memory 4260

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on PCBA 4202. Memory 4260 may be in the form of EEPROM, or NAND flash.

Additionally or alternatively, RPT device 4000 includes removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Transducers 4270

Transducers may be internal of the device, or external of the RPT device. External transducers may be located for example on or form part of the air delivery circuit, e.g. the patient interface. External transducers may be in the form of non-contact sensors such as a Doppler radar movement sensor that transmit or transfer data to the RPT device.

5.4.2.8.1 Flow

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the processor.

5.4.2.8.2 Pressure

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272, is received by the central controller processor. In one form, the signal from the pressure transducer 4272 is filtered prior to being received by the central controller 4230.

5.4.2.8.3 Motor Speed

In one form of the present technology a motor speed signal 4276 is generated. A motor speed signal 4276 is preferably provided by therapy device controller 4240. Motor speed may, for example, be generated by a speed sensor, such as a Hall effect sensor.

5.4.2.9 Data Communication Systems 4280

In one preferred form of the present technology, a data communication interface 4280 is provided, and is connected to central controller processor. Data communication interface 4280 is preferably connectable to remote external communication network 4282. Data communication interface 4280 is preferably connectable to local external communication network 4284. Preferably remote external communication network 4282 is connectable to remote external device 4286. Preferably local external communication network 4284 is connectable to local external device 4288.

In one form, data communication interface 4280 is part of processor of central controller 4230. In another form, data communication interface 4280 is an integrated circuit that is separate from the central controller processor.

In one form, remote external communication network 4282 is the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician.

Preferably local external device 4288 is a personal computer, mobile phone, tablet or remote control.

5.4.2.10 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.10.1 Display Driver 4292

A display driver 4292 receives as an input the characters, symbols, or images intended for display on the display 4294, and converts them to commands that cause the display 4294 to display those characters, symbols, or images.

5.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Communication and Diagnostic System

FIG. 7 depicts an example system 700 in which aspects of the disclosure may be implemented. This example should not be considered as limiting the scope of the disclosure or usefulness of the features described herein. In this example, system 700 includes server 710, patient devices 720, storage systems 750, as well as computing devices 760, which in one example may be associated with a clinician or device support service personnel. These devices may each communicate over network 4282. System 700 may be scaled to any size network. For example, while only three patient devices 720 are shown, system 700 may include any number of patient devices.

Each patient device 720 may include one or more devices, including RPT 4000, humidifier 5000, and patient interface 3000. In addition, each patient device 720 may be operated at remote locations and by different patients. While only controller processor 4230 and memory 4260 are shown in patient device 720, each patient device may include any of the components discussed above in connection with RPT 4000, humidifier 5000, and patient interface 3000. In addition, while patient devices 720 are shown as communicating directly over 4282, each patient device may also communicate over network 4282 via an external computing device. For example, patient device 720 may communicate with a personal computer that transmits data over network 4282.

Servers 710 may contain one or more processors 712, memory 714 and may be incorporated with other components typically present in general purpose computing devices. Memory 714 of server 710 may store information accessible by processor 712, including instructions 715 that can be executed by the processor 712. Memory 714 may also include data 718 that can be retrieved, manipulated or stored by processor 712. The memory can be of any non-transitory type capable of storing information accessible by the processor. The instructions 715 may include instructions that are directly or indirectly executed by processor 712. In that regard, the terms "instructions," "application," "steps" and "programs" can be used interchangeably herein. Functions, methods and routines of the instructions are explained in more detail below.

Data, such as diagnostic data 718 may be retrieved, stored or modified by processor 712 in accordance with the instructions 715. For instance, although the subject matter described herein is not limited by any particular data structure, the data can be stored in computer registers, in a relational database as a table having many different fields and records, or XML documents. Diagnostic data 718 may also be any information sufficient to identify or calculate relevant information, such as numbers, descriptive text, proprietary codes, pointers, references to data stored in other memories such as at other network locations. The one or more processors 712 may include conventional processors, such as a CPU, or may be a hardware-based component, such as an ASIC.

Although FIG. 7 functionally illustrates the processor, memory, and other elements of server 710, computing device 760 and patient devices 720 as each being within one block, the various components of each device may be stored within the different physical housings. For example, memory 714 may be a hard drive or other storage media located in a housing different from that of servers 710. Similarly, the storage system 750 may be part of, or be housed together with, one or more of the servers 710. Also, processor 712 may include a plurality of processors, some or all of which are located in a housing different from that of servers 710. Accordingly, references to a processor, computer, computing device, or memory will be understood to include references to a collection of processors, computers, computing devices, or memories that may or may not operate in parallel. Although some functions are described herein as taking place on a single computing device having a single processor, various aspects of the disclosure may be implemented by a plurality of computing devices communicating information with one another, such as by communicating over network 4282.

In many instances, it is preferable for patient devices 720 to communicate with network 4282 using wireless communication. However, network 4282 and intervening nodes described herein can be interconnected using various protocols and systems, such that the network can be part of the Internet, World Wide Web, specific intranets, wide area networks, local networks, or cell phone networks. The network can utilize standard communications protocols, such as Ethernet, Wi-Fi, HTTP and Bluetooth, protocols that are proprietary to one or more companies, and various combinations of the foregoing. Although certain advantages are obtained when information is transmitted or received as noted above, other aspects of the subject matter described herein are not limited to any particular manner of transmission of information.

Servers 710 may include one or more communication servers that are capable of communicating with storage system 750, computing device 760, and patient devices 720 via network 4282. As will be described in greater detail below, servers 710 may receive diagnostic data 728 from the patient devices 720 over network 4282. In response to the received diagnostic data 728, server 710 may also transmit service data 716 to patient devices 720.

Computing device 760 may be configured similarly to the servers 710, with one or more processors 762, memory 764 and instructions as described above. Each computing device may be a personal computing device intended for use by a clinician or a device support service personnel and have all of the components normally used in connection with a personal computing device such as a central processing unit (CPU), memory (e.g., RAM and internal hard drives) storing data and instructions, a display such as a display 766 (e.g., a monitor having a screen, a touch-screen, a projector, a television, or other device that is operable to display information), and user input device 768 (e.g., a mouse, keyboard, touch-screen or microphone).

A portion of the data transferred over network 4282 in accordance with aspects of the disclosure will include confidential patient information. Accordingly, system 700 may implement security measures so as to prevent unauthorized access to transmitted data. In one aspect, the connection between devices of system 700 may take the form of a VPN connection. In addition, data transmission may be based on secure socket layer (SSL) protocols. Transmitted data over network 4282 may also be encrypted using a private key infrastructure. While aspects of the system below provide for data to be presented over one or more webpages, these webpages may be presented in connection with a protected network, so that the webpages may only be accessible to authorized computing devices and users.

5.6 Example Methods

As discussed above, each patient devices 720 shown in FIG. 7 may include one or more devices, including RPT 4000, humidifier 5000, and patient interface 3000. In performing the operations described herein, patient devices 720 may implement instruction sets 726, which may include software or firmware. As discussed above in connection with FIG. 4c, RPT 4000 may include multiple controllers, such as humidity controller 5290 and therapy device controller 4240, as well as other hardware components. During operation of patient devices 720, a fault may occur in connection with one or more components. As set forth in the systems and methods described herein, these faults may be identified, and often serviced, remotely. The disclosed system allows service personnel to receive real-time notifications and diagnostic data relating to patient devices 720, so that potential problems may be identified even before a patient reports a problem with his or her patient device 720. If a problem is reported by a patient, the disclosed system provides the service personnel with visible indications of the fault, such as through the display of error icons and warning messages on a webpage or on a patient device dashboard, and provides a related report of detailed data relating to operation patient device. In this way, the service personnel may quickly determine whether the patient's reported problem is device related or not.

Each patient device 720 may generate and store diagnostic data 728. Diagnostic data 728 may include any data related to the operation of patient device 720, including data relating to faults that have occurred or are likely to occur. In one aspect, instruction sets 726 may include instructions to perform comprehensive checks of patient device 720 in order to determine whether the various components of patient device 720 are operating correctly. For example, a comprehensive check may entail checking the power supply, the air pressure being provided over patient interface 3000, as well as the temperature of one or more components of patient device 720.

In accordance with one aspect, faults may be categorized based on the components and operations that are effected, such as categorizing a fault as relating to humidification, the heated tube, the power supply, the blower, or the like. In one example, a particular fault may be categorized based on whether it requires a patient to stop using the device. In particular, patient device 720 may determine whether the detected fault is of a category that would require the patient to stop using the device, and, if so, terminating treatment to the patient. Patient device 720 may also display an error message to the patient. The error message may describe the fault that has occurred or is likely to occur.

Diagnostic data 728 is not limited to the identification of specific faults in the patient device but may also relate to the general operation and use of the device. In particular, patient device 720 may generate a log of a patient's usage of patient device 720, including identifying the time periods of use, the air pressure provided during use, air leaks that occurred during use, as well as therapeutic settings that have been used during treatment. These therapeutic settings may include various climate controls that can be set for automatic or manual adjustment. For example, a user may set the humidity, temperature, and expiratory pressure levels of the patient device 720. The patient may also set patient device 720 to a "smart start" and "smart stop" setting, in which patient device 720 will automatically begin treatment upon the patient putting on patient interface 3000 and will automatically stop treatment upon the patient taking off patient interface 3000.

Diagnostic data may also relate to a patient's condition during treatment. For example, diagnostic data 728 may include data that can be used to calculate a patient's apnea index, hypopnea index, and apnea-hyponea index, fault data, patient usage, leak data, therapy and comfort settings and order device activity and fault logs. Ambient conditions for patient device 720 may also be collected and stored as diagnostic data. For example, sensors in the patient device may be used to collect data related to the temperature and humidity of the patient device's surroundings. Such additional data can be collected to assist in diagnosing the reported problem in a more holistic way, as it presents a more complete picture of the environment within which the monitored device operates. For example, if a patient reports that the treatment starts or stops unexpectedly, information about high leak and about the fact that the "smart start/stop" function of the pressure therapy device was enabled, may explain the problem. Thus, solving patient problem is about much more than just identifying whether there is a hardware fault in the device. The reported issue may not be a problem at all and the may just be a perceived problem on the part of the patient.

In one example, diagnostic data 728 may be collected and presented as a log of events or operations that have been performed by patient device 720. The log may identify instances when a fault has occurred, including identifying the particular component or components for which a fault has occurred or is likely to occur. Details on how operational parameters can be used as an indication of a likely fault in various components of a pressure treatment device are described in the published PCT application WO 2000027457. The log may comprise a list of events and operations, as well as the date and time that each event occurred.

In accordance with one aspect, patient device 720 may transmit collected diagnostic data 728 to one or more external devices, such as servers 710 and computing device 760. The transmission of diagnostic data 728 may occur at a regular interval, such as once a day or once a week, or may be based on the occurrence of a predetermined triggering event. One such triggering event may be the occurrence of a fault, so that diagnostic data 728 is transmitted as soon as a fault is detected. In addition to data relating directly to the fault, patient device may also transmit other diagnostic data 728, including therapeutic treatment information and device settings.

The triggering event may also be based on a predetermined time period after which the patient has stopped using patient device 720. For example, instruction set 726 may indicate that diagnostic data 728 should be transmitted one hour after a patient has stopped using patient device 720. In this example, if the patient stops using patient device 720, but then resumes using it within one hour, diagnostic data 728 will not be sent. Instead, patient device 720 will wait until the patient's use of patient device 720 has stopped for the designated time period of one hour before sending diagnostic data 728. By waiting a predetermined time period before sending diagnostic data 728, instruction set 726 may prevent unnecessary transmissions of usage data that are due to brief interruptions to treatment, such as when the patient adjusts or briefly removes patient interface 3000. The predetermined time period used to trigger the transmission of diagnostic data 728 may be configurable for the particular instruction set 726 being implemented by a specific patient device.

In another example, instruction set 726 may designate a triggering event based on the amount of time that a patient has received treatment with patient device 720. This time period may also be configurable within the instruction set 726 so as to balance between limiting the amount of data that is transferred over network 4282 and achieving timeliness of diagnostic data. Instruction set 726 may also cause patient device 720 to transmit diagnostic data 728 in the event that no treatment has occurred over a predetermined time period. For example, patient device 720 may transmit diagnostic data 728 to server 710 indicating that patient device 720 has not been used in a predetermined number of hours, such as twenty-four hours.

Upon receiving diagnostic data 728 from patient device 720, server 710 may store the received data as diagnostic data 718. The stored diagnostic data at server 710 may be accessed by computing device 760, so that a user of computing device 760, such as service personnel, may monitor the condition of each patient device. Accordingly, diagnostic data 718 may be stored at server 710 in a manner that associates the diagnostic data 718 with a particular patient device 720 and a particular patient. In this way, service personnel may easily detect any issues with a particular patient device 720.

Diagnostic/fault data 728 stored at patient devices 720 may also be provided on demand to allow for immediate review. For example, immediate review of diagnostic data 728 may be needed if the user of patient device 720 calls service personnel due to a problem with the operation of patient device 720. In this instance, the service personnel may use computing device 760 to request for immediate transmittal of particular diagnostic data from patient device 720, such as all diagnostic data 728 that was collected over a particular time period, including any diagnostic data 728 relating to faults that have been detected or reported by the user.

In one aspect, servers 710 may include different types of servers, including communication servers and web servers. In this example, computing device 760 may make a request for diagnostic data 728 to a web server, which in turn transmits the request to a communication server. The communication server may then request and receive diagnostic data 728 from patient device 720. In response to the request, patient device 720 may transmit diagnostic data 728 as a log of operations and faults. The received log may then be transmitted from the web server to the communication server, where it can be accessed by computing device 760.

As set forth above, users of computing device 760, such as service personnel or clinicians, may access diagnostic data 718 that has been stored on server 710. The accessed diagnostic data 718 may be presented to computing device 760 via a web site or some other network interface. In one aspect, a user of computing device 760 may search for particular diagnostic data 718, based on patient information.

Figure 8:
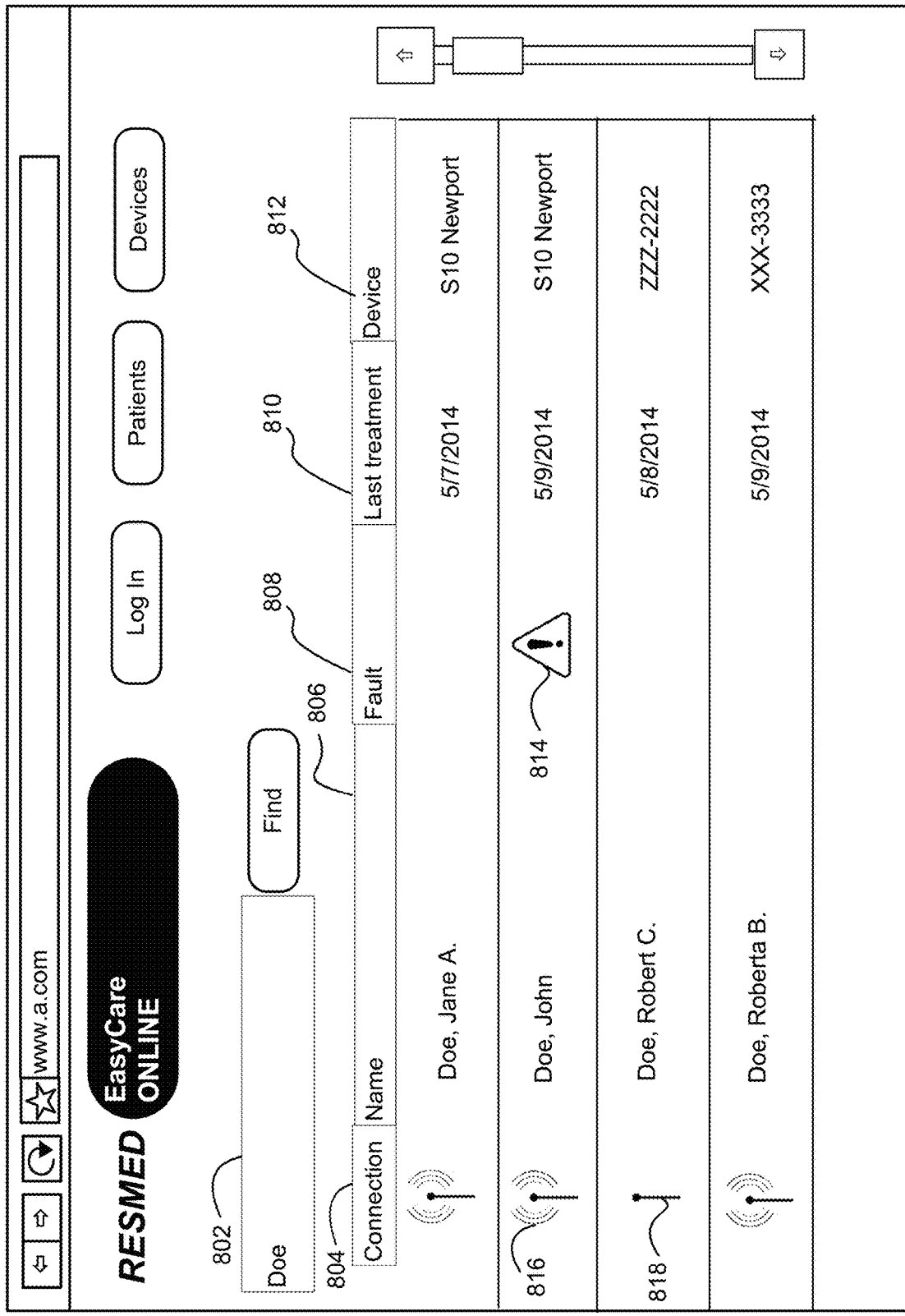

FIG. 8 shows a screenshot 800 of webpage that may be displayed in connection with a search of diagnostic data based on a patient's name. Screenshot 800 includes a search field 802, which may be used to input a search query for one or more patients. The search field may be set to search particular attributes of patients, including the patient's name, date of birth, identification number, and the like. As shown in FIG. 8, a search has been performed for patients having the name "Doe." As a result, in the proposed system clinicians can now see not only a list of their patients, but can also see, at a glance, whether any of their patients has a device with a fault such as a hardware fault. The system can also filter the patients to only show those patients that have devices with a fault or without a fault, depending on what is required by the threating clinician. In this way, the clinician could pro-actively manage their patients that have devices with problems rather than waiting for a phone call.

The results of the search are shown under column headings 804-812. The name of each patient that satisfies the search query appears under column heading 806. In addition, any device that the patient is using may be identified within the same row of the identified patient under column heading 812. The identification of the patient devices in screenshot 800 provides model numbers for each device used by the patient, however column heading 812 may include additional information about the device, including identification of the device's manufacturer and the device's serial number. Under column heading 808, an icon 814 may be displayed for any patient device that has experienced a fault or is likely to develop one. For example, icon 814 is displayed next to the name "John Doe," indicating that John Doe's model S10 Newport device has experienced a fault. As set forth above, the determination of this fault may be made by server 710 based on diagnostic data that has been transmitted from John Doe's patient device 720. Icon 814 may take any number of forms and may change based on the type of fault that has occurred. For example, icon 814 may have a variable appearance depending what component of the patient device has experienced a fault, whether the fault has caused the patient device to stop operating, and whether the patient has reported the fault. In this way, service personnel may quickly identify the nature of the problem and determine what additional actions should be considered. The service personnel may also use the appearance of icon 814, as well as any reports provided along with icon 814, to determine if an issue that has been reported by a patient is device related or not. For example, non-device related issues may include problems that arise from environmental issues or patient related issues.

In addition to the identification of faults, the webpage shown in screenshot 800 may also display other diagnostic data associated with each patient's device. For example, icons under column heading 804 provide an indication of whether a patient's device is currently connected to the network. In particular, icon 816 indicates that John Doe's device is currently connected to the network, while icon 818 indicates that Robert Doe's device is not currently connected to the network. The dates listed under column heading 810 indicate the date on which the patient last used the patient device. In accordance with one aspect, the user of computing device 760 may customize the webpage display shown in FIG. 8, so as to display additional information for each patient device.

Figure 9:
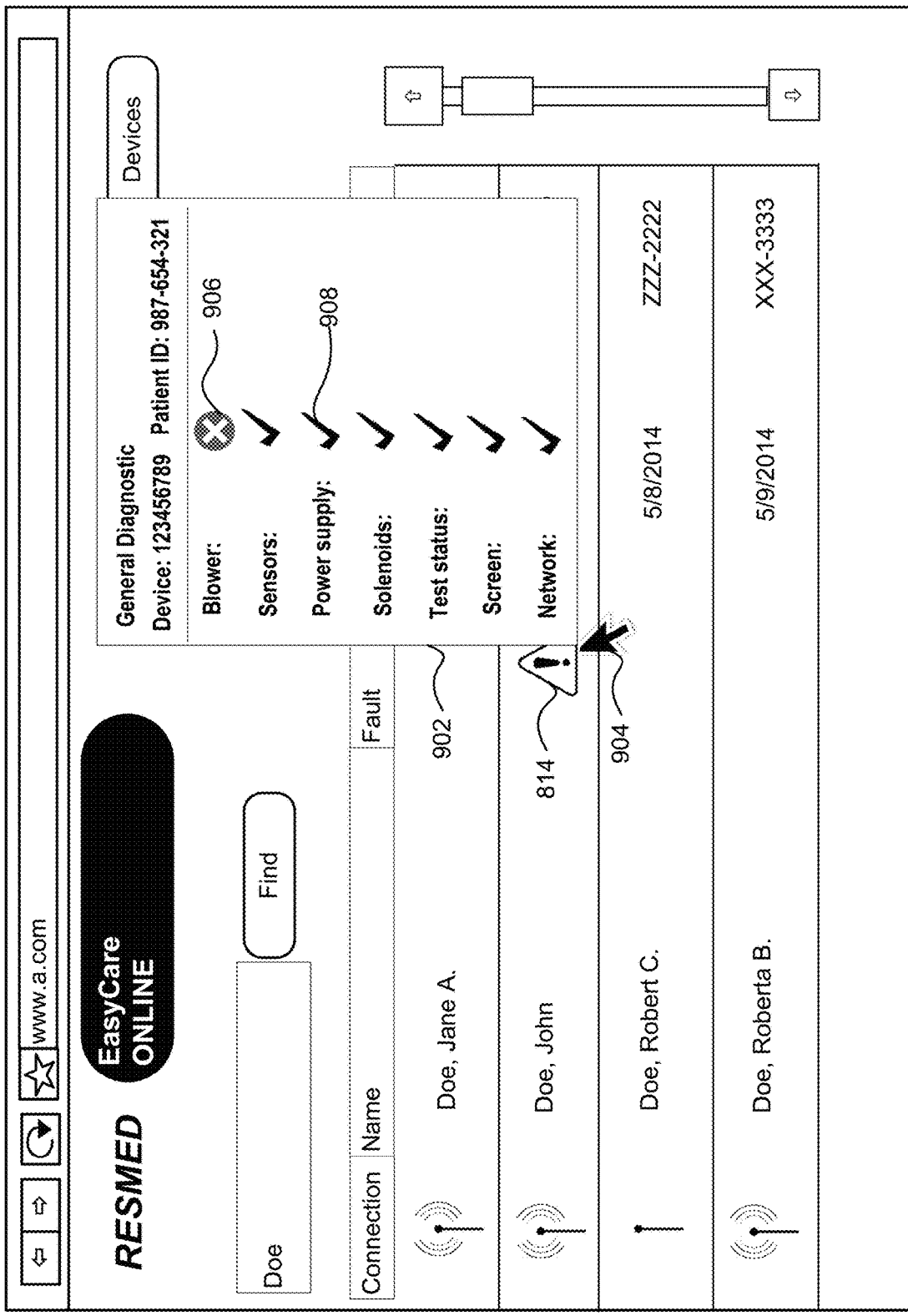

As shown in screenshot 900 of FIG. 9, the webpage may provide additional diagnostic data for particular patient devices via a popup window. For example, pop-up window 902 appears when the user moves cursor 904 over icon 814. A pop-up window may identify the specific patient device for which the fault has been detected, as well as additional information regarding the patient. For example, pop-window 902 identifies the patient, John Doe, by patient ID, 987-654-321, and identifies the patient device by a serial number, 123456789. Pop-window 902 may also display information regarding the fault that has been detected for a patient device. In particular, warning icon 906 indicates that a fault has occurred in connection with the blower of device 123456789, while check icon 908 indicates that no fault has been detected in connection with the device's power supply. In accordance with one aspect, the user may select warning icon 906 in order to receive additional details regarding the detected fault, including the specific data indicating the fault, the date and time the fault was first detected, the current setting of the patient device, etc. It should be noted that faults could be associated with any component, subsystem of functional area and the discussed examples such as a blower (flow generator) and power supply units are only examples to illustrate the system capability.

Figure 10:
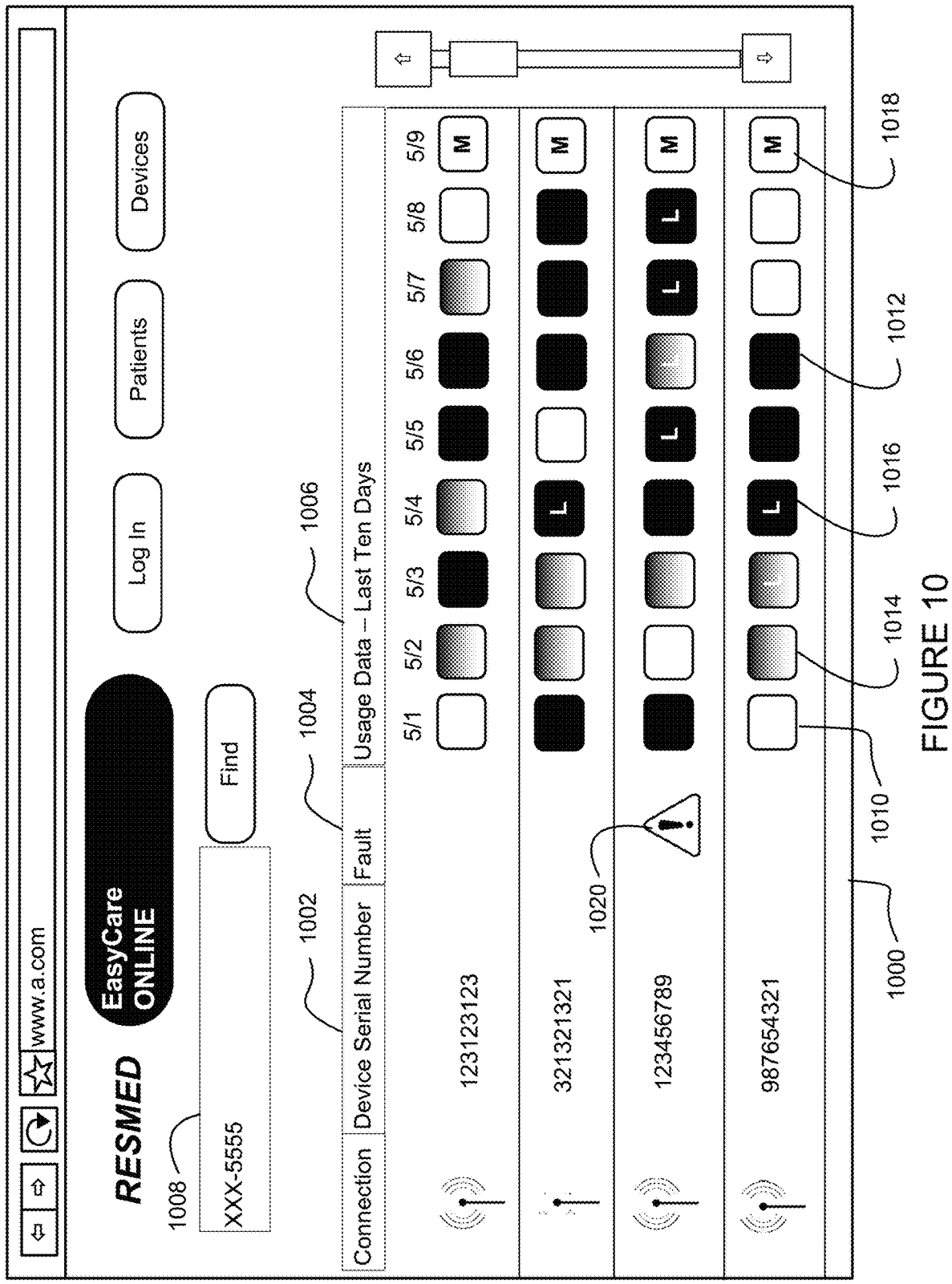

FIG. 10 shows another manner in which diagnostic data may be displayed to a user. As seen in screenshot 1000, the webpage may display diagnostic data in connection with a list of devices, rather than a list of patients. In particular, the patient device information may be presented without any specific identification of the patient, so as to maintain patient privacy with respect to service personnel. For example, diagnostic data for patient devices may be accessed based on a device identifier, such as a serial number. Under column 1002, specific patient devices may be listed by their serial numbers, with any fault indications being provided under column 1004. Additional diagnostic data may be shown in other columns. For example, the graphics shown under column heading 1006 indicate usage of each patient device over the last ten days. In particular, each usage icon 1010-1018 indicates the extent to which patient device 987654321 was used over the course of a particular day. A blank usage icon 1010 indicates that patient device 987654321 was not used on May $1^{st}$. In contrast, usage icon 1012 indicates that the patient used the patient device for at least some predetermined amount of time, such as 6 hours, on May $6^{th}$. The partially shaded usage icon 1014 indicates that the patient device was used on May $2^{nd}$, however the device was not used for the predetermined amount of time. Usage icons 1010-1018 may also indicate the manner in which the patient device was used. For example, the "L" shown in usage icon 1016 may indicate that air leak was detected during the patient's treatment on May $4^{th}$. In addition, the "M" shown in icon 1018 may designate that the device is currently being monitored or that diagnostic data has not yet been received for that day. Just as described above in connection with icon 814 of FIG. 9, a user may obtain additional information in connection with the fault indicated by icon 1020 by moving a cursor over or selecting icon 1020. In one aspect, the user may select one of the usage icons 1010-1018 in order to receive a log of diagnostic data for patient device 987654321 in connection with a particular day, as well as diagnostic data relating to the settings of one or more patient device components at the time the fault occurred. For example, the diagnostic data may identify whether automatic climate control settings were activated at the time of the fault or humidity level setting of the patient device at the time of the fault. The log may include all operations and faults that occurred over a designated time period.

In accordance with one aspect, a patient's home care provider (HCP) or the associated service personnel may use system 700 of FIG. 7 to troubleshoot a particular patient device 720. If a patient experiences a problem with the patient device 7720, the HCP may use computing device 760 to access diagnostic data 718 stored on server 710 for a particular patient device 720. Upon entering identifying information, such as a serial number, for patient device 720, server 710 may provide computing device 760 with a troubleshooting webpage, such as the webpage shown in screenshot 1100 of FIG. 11. This webpage may clearly display a message indicating whether a fault has been detected for the selected device. For example, the webpage of screenshot 1100 displays fault message 1102, which indicates that a fault has occurred. This message may indicate the nature of the fault, as well as provide instructions as to how the fault may be addressed. In particular, returning to FIG. 7, server 710 may determine if the detected fault may be addressed remotely. If so, the fault message may provide a phone number or webpage link to be used in seeking assistance with the fault. Alternatively, if it is determined that the fault cannot be addressed remotely, the message may indicate that the patient should bring the patient device into a service center for the fault to be address. If the diagnostic data 718 stored at server 710 does not indicate that a fault has occurred, a message may be provided on the webpage stating that no fault has been detected. Determining whether a fault may be addressed remotely may be based, at least in part, on whether diagnostic data 718 indicates that the fault for patient device 720 is based on a particular form of hardware failure, as some faults that are based on hardware failure will need to be addressed at a service center. In these instances, troubleshooting may end immediately, and the patient may be instructed to take the patient device in for servicing.

Alternatively, some hardware problems, such as mask fit, may also be addressed remotely by providing instructions to the HCP or patient over the troubleshooting webpage. In addition, if the fault is based on inappropriate patient device settings, or if the fault is based on the patient device's software or firmware, the fault may be addressed remotely by server 710. For example, a fault in the software of patient device 720 may be addressed by an update to instruction set 726 being transmitted to patient device 720. Accordingly, server 710 may perform troubleshooting by transmitting an update of instruction set 726 to patient device 720 over network 4282.

Figure 11:

In addition to fault message 1102, the troubleshooting webpage shown in FIG. 11 may display various information about patient device 720, including the device's model number and serial number. The troubleshooting webpage may also display the device's current settings, such as expiratory pressure relief, smart start/stop, climate control options, humidification settings, heated tube temperature settings, and the like. The troubleshooting webpage may also display environmental diagnostic data, such as the temperature and humidity of the patient's room at or near the time the fault occurred. In addition, the troubleshooting webpage may display usage data, such as the five days of usage icons 1104 displayed in screenshot 1100. As set forth above, this usage data may indicate the amount of time the patient has used the patient device, the extent to which air leaks have been detected, as well as data relating to the patient's apnea-hypopnea index. The ambient conditions for the patient device may also be displayed on the troubleshooting webpage. Identification of various components being used by the patient, such as the type of humidifier 5000 and the type of patient interface 3000, may also be identified on the troubleshooting webpage. This information may be used by an HCP to determine the manner in which the fault is to be addressed. For example, a fault associated with an air leak may be addressed in different ways, depending on the type of mask that is being used by the patient. As shown in FIG. 11, information may be provided on the troubleshooting webpage regarding the type of mask being used, along with recent leak information for patient device 720. The mask information may be used as indicators relating to unexpected stoppage in therapy or poor mask fit and may include identification of the design, size, and brand of the mask being used with patient device 720.

Using the troubleshooting webpage, an HCP, may identify what has caused the fault and adjust the settings of patient device 720 in order to address the problem. In one aspect, an HCP may adjust the patient's therapy and the settings of patient device 720 by inputting the adjustments directly into the troubleshooting webpage. For example, an HCP may use the troubleshooting webpage in FIG. 11 to adjust the humidity level of device 123456789 from level 5 to level 3. The altering the humidity level in the troubleshooting webpage may be received by server 710 shown in FIG. 7. In turn server 710 may transmit a humidity alteration command to patient device 720. Patient device 720 may then alter its humidity level in response to the received command.

In accordance with one aspect, server 710 may transmit diagnostic data 718 to computing device 760 in the form of a diagnostic log of operations and faults. In one example, the user of computing device 760 may request a diagnostic log from server 710 for one or more patient devices 720. This request may specify the type of diagnostic data that is to be included in the log. For example, user, through computing device 760, may request a diagnostic log for all faults that have occurred for a particular patient device. Alternatively, the user may request a log of all diagnostic data related to a particular component or set of components, such as humidifier 5000. In this way, the user of computing device may be provided with a specific set of information that can be used in addressing problems that have occurred in connection with patient device 720.

Figure 12:
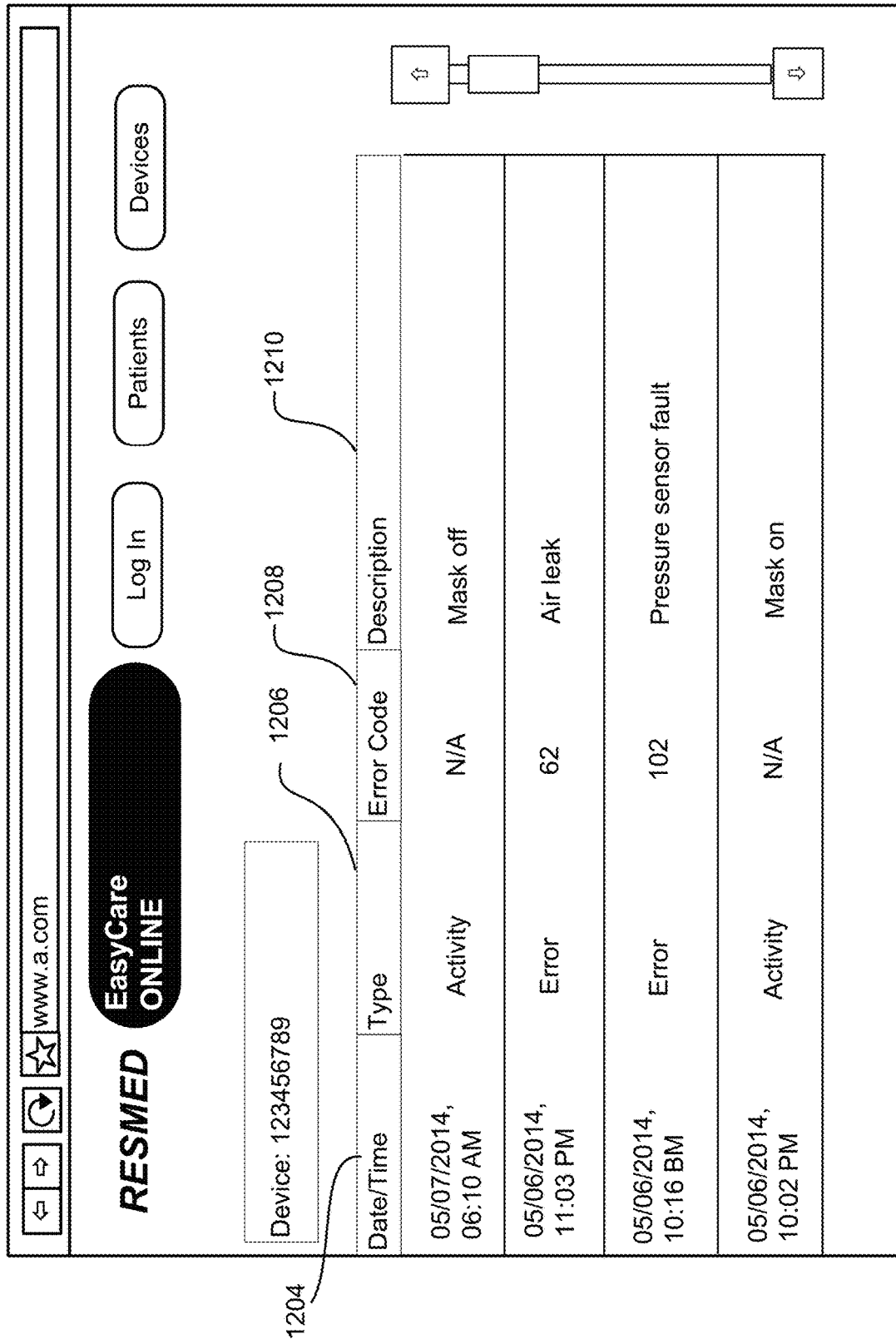

Screenshot 1200 of FIG. 12 shows an example diagnostic log that may be displayed on a computing device. In this example, the computing device has requested a log of all activities and faults that have occurred over the last 24 hours on the patient device having serial number 123456789. The dates and time identified under column heading 1204 indicate the date and time of each fault that has occurred, while the information under column heading 1206 designates whether the entry relates to an activity or a fault. As provided under column heading 1208, an error code may be identified for each fault. This allows service personnel to identify the specific type of fault that has occurred. In addition, each log entry may include a description, as provided under column heading 1210. The description of the log entry may identify the activity that has occurred, such as the user putting on or taking off the device's mask, or may provide information about a fault that has occurred.

In accordance with one aspect, the diagnostic log presented to a user may be expanded or filtered based on user input. For example, the diagnostic log shown in FIG. 12 may be expanded to include activities and faults that have occurred for device 123456789 over a long period of time, such as the last 30 days. The diagnostic log may also be filtered so that it only shows a particular type of activity or so that it only shows faults that have occurred on the patient device. In this way, a user may easily access the information needed in servicing a patient device.

In accordance with one aspect, server 710 of FIG. 7 may transmit a fault indication to computing device 760 as soon as a fault has been detected in one of the patient devices 720. Accordingly, instead of waiting for a request for diagnostic data, server 710 may push a notification to computing device 760 as soon as the diagnostic data for patient device 720 indicates that a fault has occurred. This notification may occur as an SMS message, e-mail, or some other form of push notifications. In this way, HCPs or service personnel may be immediately notified of problems with patient devices 720. In one example, a push notification will only be provided for certain types of faults, such has faults that may negatively affect a patient's treatment. Accordingly, upon receiving an indication of a fault from patient device 720, server 710 may determine whether the identified fault is one for which a push notification is to be transmitted to computing device 760.

FIG. 13 is a flow diagram 1300 that may be performed by a patient device of the disclosed system described above. In block 1302, the patient device collects diagnostic data in accordance with an instruction set. As set forth above, diagnostic data may include operations and faults that occur in connection with the patient device, as well as identification of settings for the patient device. While collecting the diagnostic data, patient device determine whether a triggering event has occurred (Block 1304). Once a triggering event has been identified, the patient device may transmit at least a portion of the diagnostic data over a network, such as transmitting the diagnostic data to a server (Block 1306). As set forth above, a triggering event may be based on actions performed by the patient or operations performed by the patient device. For example a triggering event may be based on a determination that the patient has stopped using the patient device for a predetermined period of time. A triggering event may also include receiving a request for diagnostic data from an external device, such as a server. The request or trigger event may require the patient device to transmit a particular portion of the collected diagnostic data. For example, the patient device may transmit all diagnostic data that has been collected since the last transmission.

The patient device may also determine whether service data has been received (Block 1308). Service data may include information provided by a remote service in attempt to address an identified fault. For example, service data may include an update to the patient device's software or firmware or an update to one or more of the patient device's settings. If service data has not been received, the patient device may continue to collect diagnostic data and determine whether a triggering event has occurred in accordance with Blocks 1302 and 1304. However, if service data has been received, the patient device may update itself in accordance with the received service data (Block 1310). The update may include adding new instruction sets, altering current instruction sets, or altering the settings of the patient device. The patient device may then continue to collect diagnostic data (Block 1302) and transmit diagnostic data (Block 1306) in accordance with the current instruction set, which may include updates instructions.

FIG. 14 shows flow diagram 1400 that may be performed by computing devices of the disclosed system, including server 710 of system 700. In Block 1402, a server may receive a query for diagnostic data associated with one or more patient devices. For example, as described above, server 710 may receive a query from computing device 760 seeking data in connection with a particular patient device or set of patient devices. This query may seek identification of all patient devices that meet one or more criteria provided by a user of computing device 760. The criteria may be based on any number of aspects or features of the patient device, including devices that have experienced faults over some defined time period. In this way, the user of computing device 760 may be made aware of faults shortly after they occur, possibly even before the patient has noted the problem or has notified the user of the problem. The server may access diagnostic data in response to the received query (Block 1404), and may determine whether a fault has occurred in connection with the one or more patient devices (Block 1406).

The server may respond to the query by transmitting diagnostic data for one or more patient devices, including identification of any faults that have occurred for the one or more patient devices (Block 1408). The transmission of diagnostic data may occur over one or more webpages, such as the webpages shown in FIGS. 8-12. As set forth above, the webpage may identify specific faults that have occurred for one or more patient devices, as well as potential actions that should be taken in connection with each identified fault.

The server may then receive a request for service data to be transmitted to one or more patient devices (Block 1410). The transmitted service data may take the form of a command to adjust to one or more device settings or updates to the patient device instruction set. For example, in addressing an identified fault of condensation in the conduit of a patient device, the user of computing device 760 may select specific setting changes to be transmitted as service data to the patient device, so as to adjust the level of humidification being provided by the humidifier of the patient device. Upon receiving the request of Block 1410, the server may access or otherwise generate service data (Block 1412) and transmit the service data to the patient devices identified in the received request (Block 1414). The server may also determine if the transmission of the service was successful (Block 1416). For example, the server may receive from each patient device either an error notification or a message that the service data was successfully implemented. If an error occurred in the transmission of the service data, the server may transmit the service data again for each patient device for which the error occurred (Block 1414). However, if the transmission is successful, the server may revise the stored diagnostic data to indicate that the one or more patient devices have implemented the transmitted service data (Block 1418).

While the operations set forth in FIGS. 13 and 14 may each be performed by a single device, the operations may alternatively be performed by more than one device. For example, a patient device may communicate with a personal computer over a wireless network, so that the personal computer may perform one or more of the operations described above. The server referenced in connection with FIGS. 14 and 9 may also include a plurality of servers, with each server performing one or more of the operations described above. Various operations may be added or removed from flow diagrams 1300 and 1400. For example, a system in accordance with the current disclosure may perform the methods associated with flow diagram 1400 without performing the procedures described in Block 1412 to Block 1418. In addition, various operations need not be performed in the same order as set forth in flow diagrams 1300 and 1400.

5.7 Glossary

In certain forms of the present technology, one or more of the following definitions may apply. In other forms of the present technology, alternative definitions may apply.

5.7.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.7.2 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.7.3 Aspects of a Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: A conduit that directs an axis of flow of air to change direction through an angle. In one form, the angle may be approximately 90 degrees. In another form, the angle may be less than 90 degrees. The conduit may have an approximately circular cross-section. In another form the conduit may have an oval or rectangular cross-section.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. Preferably the headgear comprises a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a patient interface plenum chamber will be taken to mean a portion of a patient interface having walls enclosing a volume of space, such as for a full-face mask (e.g., nose and mouth mask), a nasal mask or a nasal pillow, the volume having air therein pressurised above atmospheric pressure in use by the patient. A shell may form part of the walls of a patient interface plenum chamber. In one form, a region of the patient's face abuts one of the walls of the plenum chamber, such as via a cushion or seal.

Seal: The noun form ("a seal") will be taken to mean a structure or barrier that intentionally resists the flow of air through the interface of two surfaces. The verb form ("to seal") will be taken to mean to resist a flow of air.

Shell: A shell will preferably be taken to mean a curved structure having bending, tensile and compressive stiffness, for example, a portion of a mask that forms a curved structural wall of the mask. Preferably, compared to its overall dimensions it is relatively thin. In some forms, a shell may be faceted. Preferably such walls are airtight, although in some forms they may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel: (noun) A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. Preferably there is little or no leak flow of air from the swivel in use.

Tie: A tie will be taken to be a structural component designed to resist tension.

Vent: (noun) the structure that allows a deliberate controlled rate leak of air from an interior of the mask, or conduit to ambient air, to allow washout of exhaled carbon dioxide ($CO_2$) and supply of oxygen ($O_2$).

5.8 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

| LIST OF REFENCE NUMBERS | |
|---|---|
| system | 700 |
| server | 710 |
| processor | 712 |
| memory | 714 |
| instruction | 715 |
| service data | 716 |
| diagnostic data | 718 |
| patient device | 720 |
| instruction set | 726 |
| diagnostic data | 728 |
| storage system | 750 |
| computing device | 760 |
| processor | 762 |
| memory | 764 |
| display | 766 |
| user input device | 768 |
| screenshot | 800 |
| search field | 802 |
| column heading | 804-812 |
| icons | 814-818 |
| screenshot | 900 |
| window | 902 |
| cursor | 904 |
| warning icon | 906 |
| check icon | 908 |
| patient | 1000 |
| screenshot | 1000 |
| column | 1002 |
| column | 1004 |
| column heading | 1006 |
| blank usage icon | 1010 |
| icons | 1012-1020 |
| screenshot | 1100 |
| fault message | 1102 |
| usage icon | 1104 |
| screenshot | 1200 |
| column headings | 1204-1210 |
| patient interface | 3000 |
| seal-forming structure | 3100 |
| plenum chamber | 3200 |
| perimeter | 3210 |
| vent | 3400 |
| connection port | 3600 |
| RPT device | 4000 |
| external housing | 4010 |
| upper portion of external housing | 4012 |
| lower portion of external housing | 4014 |
| panel | 4015 |
| chassis | 4016 |
| handle | 4018 |
| pneumatic block | 4020 |
| pneumatic component | 4100 |
| air filter | 4110 |
| inlet air filter | 4112 |
| outlet air filter | 4114 |
| muffler | 4120 |
| inlet muffler | 4122 |
| outlet muffler | 4124 |
| pressure device | 4140 |
| controllable pressure device | 4140 |
| blower | 4142 |
| controllable blower | 4142 |
| brushless DC motor | 4144 |
| back valve | 4160 |
| air circuit | 4170 |
| supplemental oxygen | 4180 |
| electrical component | 4200 |
| RPT device electrical component | 4200 |
| PCBA | 4202 |
| electrical power supply | 4210 |
| input device | 4220 |
| central controller | 4230 |
| clock | 4232 |
| therapy device controller | 4240 |
| protection circuit | 4250 |
| memory | 4260 |
| transducer | 4270 |
| pressure transducer | 4272 |
| pressure sensor | 4271 |

-continued

| LIST OF REFENCE NUMBERS | |
|---|---|
| motor speed signal | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| pressure control module | 4330 |
| humidifier | 5000 |
| humidifier controller | 5250 |
| humidity controller | 5290 |
| patient device | 7720 |

The invention claimed is:

1. A method comprising:
collecting, by one or more processors, diagnostic data relating to operation of a patient respiratory therapy device, wherein the diagnostic data identifies a presence of a fault in connection with the patient respiratory therapy device;
determining, by the one or more processors, that a triggering event has occurred for which the diagnostic data is to be transmitted over a network, wherein the triggering event is based on a determination that a patient has stopped using the patient respiratory therapy device for a predetermined period of time;
transmitting, by the one or more processors, the diagnostic data over the network to one or more computing devices, wherein at least a first portion of the diagnostic data is configured so that the presence of the fault is identifiable by a computing device;
receiving, by the one or more processors, service data that addresses an identified fault from the one or more computing devices; and
performing, by the one or more processors, one or more operations in accordance with the service data that has been received.

2. The method of claim 1, wherein the service data comprises a first portion and a second portion, both portions being associated with different components of the patient respiratory therapy device.

3. The method of claim 1, further comprising:
sending to a remote computing device data indicating whether any patient has a device with a fault.

4. The method of claim 1, wherein at least a portion of the diagnostic data relates to at least one of the following: a patient's apnea index, a patient's hypopnea index, a patient's apnea-hypopnea index, fault data, patient usage, leak data, ambient humidity data, therapy and comfort settings, or device activity.

5. The method of claim 1, further comprising:
sending, by the one or more processors, an indication to the one or more computing devices that the service data was successfully transmitted.

6. The method of claim 1, wherein the service data includes a command to adjust one or more settings of the patient respiratory therapy device.

7. The method of claim 1, wherein the diagnostic data includes an indication of one or more settings of the patient respiratory therapy device at a time at which the identified fault occurred.

8. The method of claim 1, wherein the triggering event is further based on an amount of time that the patient has received treatment with the patient respiratory therapy device.

9. The method of claim 1, further comprising:
receiving, by the one or more computing devices, the diagnostic data from the one or more processors;
identifying, by the one or more computing devices, the fault based on the first portion of the diagnostic data; and
transmitting, by the one or more computing devices, the service data to the one or more processors.

10. The method of claim 8, further comprising:
transmitting, by the one or more computing devices, the identified fault with the patient respiratory therapy device to a remote computing device.

11. The method of claim 10, wherein transmitting the identified fault comprises providing an icon for display on the remote computing device.

12. The method of claim 11, wherein the icon has a variable appearance that varies based on a type of fault that has occurred.

13. The method of claim 10, wherein transmitting the identified fault further comprises providing usage icons for display on the remote computing device, wherein the usage icons indicate an extent to which the patient respiratory therapy device was used.

14. The method of claim 1, wherein the diagnostic data includes leak information and identification of a type of mask being used with the patient respiratory therapy device.

* * * * *